(12) United States Patent
Davis et al.

(10) Patent No.: US 12,310,567 B2
(45) Date of Patent: May 27, 2025

(54) MICRO-FABRICATED MEDICAL DEVICE HAVING A NON-HELICAL CUT ARRANGEMENT

(71) Applicant: SCIENTIA VASCULAR, INC., West Valley City, UT (US)

(72) Inventors: Clark C. Davis, Holladay, UT (US); John A. Lippert, Park City, UT (US)

(73) Assignee: SCIENTIA VASCULAR, INC., West Valley City, UT (US)

( * ) Notice: Subject to any disclaimer, the term of this patent is extended or adjusted under 35 U.S.C. 154(b) by 164 days.

(21) Appl. No.: 17/752,600

(22) Filed: May 24, 2022

(65) Prior Publication Data
US 2022/0280147 A1 Sep. 8, 2022

Related U.S. Application Data

(62) Division of application No. 16/616,139, filed as application No. PCT/US2018/034756 on May 25, 2018, now Pat. No. 11,369,351.
(Continued)

(51) Int. Cl.
*A61B 17/00* (2006.01)
*A61M 25/00* (2006.01)
*A61M 25/09* (2006.01)

(52) U.S. Cl.
CPC ............ *A61B 17/00234* (2013.01); *A61B 2017/00309* (2013.01); *A61M 2025/0042* (2013.01);
(Continued)

(58) Field of Classification Search
CPC .............. A61B 17/00; A61B 17/00234; A61B 2017/1205; A61B 2017/00309; A61M 2025/0042; A61F 2/95; A61F 2/958
See application file for complete search history.

(56) References Cited

U.S. PATENT DOCUMENTS

| 2,022,065 | A | 11/1935 | Wappler |
| 2,187,299 | A | 1/1940 | Otto |

(Continued)

FOREIGN PATENT DOCUMENTS

| AU | 07230/40 B2 | 8/2000 |
| AU | 733966 B2 | 5/2001 |

(Continued)

OTHER PUBLICATIONS

Final Office Action received for U.S. Appl. No. 17/154,777, mailed on Apr. 17, 2024, 17 pages.
(Continued)

*Primary Examiner* — Vi X Nguyen
(74) *Attorney, Agent, or Firm* — Workman Nydegger

(57) ABSTRACT

The present disclosure relates to interventional devices such as catheters and guidewire devices having micro-fabricated features for providing flexibility while maintaining good torquability. An interventional device includes an elongated member having an arrangement of fenestrations which define a plurality of axially extending beams coupling a plurality of circumferentially extending rings. The fenestrations are arranged so that the resulting beams form a distributed, non-helical and non-linear pattern along the length of the elongated member. The pattern of fenestrations thereby minimizes or eliminates preferred bending axes.

17 Claims, 9 Drawing Sheets

Related U.S. Application Data

(60) Provisional application No. 62/595,425, filed on Dec. 6, 2017, provisional application No. 62/511,605, filed on May 26, 2017.

(52) U.S. Cl.
CPC .................. *A61M 25/0054* (2013.01); *A61M 2025/09091* (2013.01)

(56) References Cited

U.S. PATENT DOCUMENTS

| | | |
|---|---|---|
| 3,183,702 A | 5/1965 | Zittell |
| 3,572,334 A | 3/1971 | Petterson |
| 3,612,058 A | 10/1971 | Ackerman |
| 3,709,271 A | 1/1973 | Flory |
| 3,782,233 A | 1/1974 | Helm |
| 3,920,058 A | 11/1975 | Walker |
| 4,163,406 A | 8/1979 | Crawford |
| 4,239,069 A | 12/1980 | Zimmerman |
| 4,416,312 A | 11/1983 | Oestberg |
| 4,688,540 A | 8/1987 | Ono |
| 4,719,924 A | 1/1988 | Crittenden et al. |
| 4,801,297 A | 1/1989 | Mueller |
| 4,846,186 A | 7/1989 | Box et al. |
| 4,895,168 A | 1/1990 | Machek |
| 4,989,608 A | 2/1991 | Ratner |
| 5,047,045 A | 9/1991 | Arney et al. |
| 5,069,217 A | 12/1991 | Fleischhacker, Jr. |
| 5,084,022 A | 1/1992 | Claude |
| 5,095,915 A | 3/1992 | Engelson |
| 5,102,390 A | 4/1992 | Crittenden et al. |
| 5,144,959 A | 9/1992 | Gambale et al. |
| 5,147,317 A | 9/1992 | Shank et al. |
| 5,154,725 A | 10/1992 | Leopold |
| 5,174,302 A | 12/1992 | Palmer |
| 5,315,996 A | 5/1994 | Lundquist |
| 5,326,374 A | 7/1994 | Ilbawi et al. |
| 5,345,945 A | 9/1994 | Hodgson et al. |
| 5,366,464 A | 11/1994 | Belknap |
| 5,372,587 A | 12/1994 | Hammerslag et al. |
| 5,381,782 A | 1/1995 | Delarama et al. |
| 5,382,259 A | 1/1995 | Phelps et al. |
| 5,385,152 A | 1/1995 | Abele et al. |
| 5,437,288 A | 7/1995 | Schwartz et al. |
| 5,441,483 A | 8/1995 | Avitall |
| D363,544 S | 10/1995 | Rowland et al. |
| D363,776 S | 10/1995 | Rowland et al. |
| 5,480,382 A | 1/1996 | Hammerslag et al. |
| 5,506,682 A | 4/1996 | Pryor |
| 5,507,751 A | 4/1996 | Goode et al. |
| 5,551,444 A | 9/1996 | Finlayson |
| 5,554,114 A | 9/1996 | Wallace et al. |
| 5,569,218 A | 10/1996 | Berg |
| 5,573,520 A | 11/1996 | Schwartz et al. |
| 5,573,867 A | 11/1996 | Zafred et al. |
| 5,606,981 A | 3/1997 | Tartacower et al. |
| 5,659,205 A | 8/1997 | Weisser |
| 5,673,707 A | 10/1997 | Chandrasekaran |
| 5,676,659 A | 10/1997 | McGurk |
| 5,685,568 A | 11/1997 | Pirrello |
| 5,685,868 A | 11/1997 | Lundquist |
| 5,690,120 A | 11/1997 | Jacobsen et al. |
| 5,706,826 A | 1/1998 | Schwager |
| 5,741,429 A | 4/1998 | Donadio et al. |
| 5,746,701 A | 5/1998 | Noone |
| 5,792,154 A | 8/1998 | Doan et al. |
| 5,797,857 A | 8/1998 | Obitsu |
| 5,800,454 A | 8/1998 | Jacobsen et al. |
| 5,833,631 A | 11/1998 | Nguyen |
| 5,833,632 A | 11/1998 | Jacobsen et al. |
| 5,842,461 A | 11/1998 | Azuma |
| 5,860,963 A | 1/1999 | Azam et al. |
| 5,876,356 A | 3/1999 | Viera et al. |
| 5,911,715 A | 6/1999 | Berg et al. |
| 5,911,717 A | 6/1999 | Jacobsen et al. |
| 5,916,194 A | 6/1999 | Jacobsen et al. |
| 5,931,830 A | 8/1999 | Jacobsen et al. |
| 5,954,672 A | 9/1999 | Schwager |
| 6,004,279 A | 12/1999 | Crowley et al. |
| 6,014,919 A | 1/2000 | Jacobsen |
| 6,017,319 A | 1/2000 | Jacobsen et al. |
| 6,022,343 A | 2/2000 | Johnson et al. |
| 6,022,369 A | 2/2000 | Jacobsen et al. |
| 6,027,526 A | 2/2000 | Limon et al. |
| 6,027,863 A | 2/2000 | Donadio, III |
| 6,033,288 A | 3/2000 | Weisshaus et al. |
| 6,033,394 A | 3/2000 | Vidlund et al. |
| 6,056,702 A | 5/2000 | Lorenzo |
| 6,063,101 A | 5/2000 | Jacobsen et al. |
| 6,110,164 A | 8/2000 | Vidlund |
| 6,132,389 A | 10/2000 | Cornish et al. |
| 6,139,511 A | 10/2000 | Huter et al. |
| D435,909 S | 1/2001 | Ogino et al. |
| 6,168,570 B1 | 1/2001 | Ferrera |
| 6,179,828 B1 | 1/2001 | Mottola et al. |
| 6,183,410 B1 | 2/2001 | Jacobsen et al. |
| 6,183,420 B1 | 2/2001 | Douk et al. |
| 6,214,042 B1 | 4/2001 | Jacobsen et al. |
| 6,228,073 B1 | 5/2001 | Noone et al. |
| 6,245,030 B1 | 6/2001 | Dubois et al. |
| 6,251,086 B1 | 6/2001 | Cornelius et al. |
| 6,260,458 B1 | 7/2001 | Jacobsen et al. |
| 6,261,246 B1 | 7/2001 | Pantages et al. |
| 6,273,881 B1 | 8/2001 | Kiemeneij |
| 6,302,870 B1 | 10/2001 | Jacobsen et al. |
| 6,306,105 B1 | 10/2001 | Rooney et al. |
| 6,346,091 B1 | 2/2002 | Jacobsen et al. |
| 6,356,791 B1 | 3/2002 | Westlund et al. |
| 6,402,706 B2 | 6/2002 | Richardson et al. |
| 6,428,489 B1 | 8/2002 | Jacobsen et al. |
| 6,431,039 B1 | 8/2002 | Jacobsen et al. |
| 6,436,056 B1 | 8/2002 | Wang et al. |
| 6,440,088 B1 | 8/2002 | Jacobsen et al. |
| 6,458,867 B1 | 9/2002 | Wang et al. |
| 6,464,651 B1 | 10/2002 | Hiejima et al. |
| 6,492,615 B1 | 12/2002 | Flanagan |
| 6,494,894 B2 | 12/2002 | Mirarchi |
| 6,527,732 B1 | 3/2003 | Strauss et al. |
| 6,527,746 B1 | 3/2003 | Oslund et al. |
| 6,553,880 B2 | 4/2003 | Jacobsen et al. |
| 6,554,820 B1 | 4/2003 | Wendlandt et al. |
| 6,558,355 B1 | 5/2003 | Metzger et al. |
| 6,579,246 B2 | 6/2003 | Jacobsen et al. |
| 6,602,207 B1 | 8/2003 | Mam et al. |
| 6,606,985 B2 | 8/2003 | Negishi |
| 6,610,046 B1 | 8/2003 | Usami et al. |
| 6,627,724 B2 | 9/2003 | Meijs et al. |
| 6,652,508 B2 | 11/2003 | Griffin et al. |
| 6,671,560 B2 | 12/2003 | Westlund et al. |
| 6,766,720 B1 | 7/2004 | Jacobsen et al. |
| 6,805,676 B2 | 10/2004 | Klint |
| 6,866,642 B2 | 3/2005 | Kellerman et al. |
| RE39,018 E | 3/2006 | Azuma et al. |
| 7,024,885 B2 | 4/2006 | Villalobos |
| 7,097,624 B2 | 8/2006 | Campion et al. |
| 7,110,910 B1 | 9/2006 | Deffenbaugh et al. |
| 7,128,718 B2 | 10/2006 | Hojeibane et al. |
| 7,172,587 B2 | 2/2007 | Poole et al. |
| 7,182,735 B2 | 2/2007 | Shireman et al. |
| 7,276,062 B2 | 10/2007 | McDaniel et al. |
| 7,338,345 B2 | 3/2008 | Fujinami |
| 7,421,929 B2 | 9/2008 | French |
| 7,494,474 B2 | 2/2009 | Richardson et al. |
| 7,507,246 B2 | 3/2009 | McGuckin et al. |
| D598,094 S | 8/2009 | Alber |
| 7,621,880 B2 | 11/2009 | Ryan et al. |
| 7,637,875 B2 | 12/2009 | Itou |
| 7,641,622 B2 | 1/2010 | Satou et al. |
| D611,596 S | 3/2010 | Kousai et al. |
| 7,670,302 B2 | 3/2010 | Griffin et al. |
| 7,699,792 B2 | 4/2010 | Hofmann et al. |
| 7,722,545 B2 | 5/2010 | Bertsch |
| 7,722,552 B2 | 5/2010 | Aimi et al. |

(56) References Cited

U.S. PATENT DOCUMENTS

| | | |
|---|---|---|
| 7,744,545 B2 | 6/2010 | Aimi et al. |
| 7,747,314 B2 | 6/2010 | Parins et al. |
| 7,753,859 B2 | 7/2010 | Kinoshita et al. |
| 7,766,896 B2 | 8/2010 | Kornkven et al. |
| 7,769,839 B2 | 8/2010 | Boivie et al. |
| 7,785,273 B2 | 8/2010 | Eskuri |
| 7,789,839 B2 | 9/2010 | Lupton |
| 7,806,837 B2 | 10/2010 | Rasmussen et al. |
| 7,878,984 B2 | 1/2011 | Jacobsen et al. |
| 7,883,474 B1 | 2/2011 | Mirigian et al. |
| 7,914,467 B2 | 3/2011 | Layman et al. |
| 7,942,832 B2 | 5/2011 | Kanuka et al. |
| 7,967,762 B2 | 6/2011 | Corl et al. |
| 7,989,042 B2 | 8/2011 | Obara et al. |
| 8,007,434 B2 | 8/2011 | Olson |
| 8,043,314 B2 | 10/2011 | Noriega et al. |
| 8,048,004 B2 | 10/2011 | Davis et al. |
| 8,092,444 B2 | 1/2012 | Lentz et al. |
| 8,105,246 B2 | 1/2012 | Voeller et al. |
| 8,128,579 B2 | 3/2012 | Chen et al. |
| 8,128,580 B2 | 3/2012 | Fujimagari et al. |
| 8,137,293 B2 | 3/2012 | Zhou et al. |
| 8,167,821 B2 | 4/2012 | Sharrow |
| 8,257,279 B2 | 9/2012 | Jacobsen |
| 8,292,827 B2 | 10/2012 | Musbach et al. |
| 8,292,828 B2 | 10/2012 | Uihlein |
| 8,357,140 B2 | 1/2013 | Majercak et al. |
| 8,376,865 B2 | 2/2013 | Forster et al. |
| 8,376,961 B2 | 2/2013 | Layman et al. |
| 8,377,056 B2 | 2/2013 | Oyola et al. |
| 8,409,114 B2 | 4/2013 | Parins |
| 8,409,169 B1 | 4/2013 | Moss |
| 8,444,577 B2 | 5/2013 | Bunch et al. |
| 8,454,535 B2 | 6/2013 | Majercak et al. |
| 8,460,213 B2 | 6/2013 | Northrop |
| 8,465,469 B2 | 6/2013 | Brightbill |
| 8,468,919 B2 | 6/2013 | Christian et al. |
| 8,500,658 B2 | 8/2013 | Boyle et al. |
| 8,517,959 B2 | 8/2013 | Kurosawa et al. |
| 8,535,243 B2 | 9/2013 | Shireman |
| 8,540,648 B2 | 9/2013 | Uihlein |
| 8,540,668 B2 | 9/2013 | Griffin et al. |
| 8,551,020 B2 | 10/2013 | Chen et al. |
| 8,551,021 B2 | 10/2013 | Voeller et al. |
| 8,556,914 B2 | 10/2013 | Vrba |
| 8,585,643 B2 | 11/2013 | Vo et al. |
| 8,622,931 B2 | 1/2014 | Teague et al. |
| 8,622,933 B2 | 1/2014 | Maki et al. |
| 8,636,270 B2 | 1/2014 | Ostrovsky |
| 8,728,075 B2 | 5/2014 | Wu et al. |
| 8,758,269 B2 | 6/2014 | Miyata et al. |
| 8,784,337 B2 | 7/2014 | Voeller et al. |
| 8,795,202 B2 | 8/2014 | Northrop et al. |
| 8,795,254 B2 | 8/2014 | Layman et al. |
| 8,821,477 B2 | 9/2014 | Northrop et al. |
| 8,870,790 B2 | 10/2014 | Davis et al. |
| 8,900,163 B2 | 12/2014 | Jacobsen et al. |
| 8,915,865 B2 | 12/2014 | Jacobsen et al. |
| 8,932,235 B2 | 1/2015 | Jacobsen et al. |
| 8,936,558 B2 | 1/2015 | Jacobsen et al. |
| 8,939,916 B2 | 1/2015 | Jacobsen et al. |
| 8,956,310 B2 | 2/2015 | Miyata et al. |
| 9,011,511 B2 | 4/2015 | Gregorich et al. |
| 9,067,332 B2 | 6/2015 | Lippert et al. |
| 9,067,333 B2 * | 6/2015 | Lippert ............ A61M 25/0045 |
| 9,072,873 B2 | 7/2015 | Lippert et al. |
| 9,072,874 B2 | 7/2015 | Northrop et al. |
| D742,000 S | 10/2015 | Kanazawa |
| 9,162,040 B2 | 10/2015 | Vo et al. |
| 9,227,037 B2 | 1/2016 | Northrop |
| 9,254,143 B2 | 2/2016 | Huynh et al. |
| 9,364,589 B2 | 6/2016 | Cage et al. |
| 9,375,234 B2 | 6/2016 | Vrba |
| 9,433,762 B2 | 9/2016 | Griffin et al. |
| 9,439,557 B2 | 9/2016 | Boulais |
| 9,550,013 B2 | 1/2017 | Kawasaki |
| 9,616,195 B2 | 4/2017 | Lippert et al. |
| 9,623,212 B2 | 4/2017 | Tano et al. |
| 9,662,798 B2 | 5/2017 | Christian et al. |
| 9,700,702 B2 | 7/2017 | Tano et al. |
| 9,808,595 B2 | 11/2017 | Turnlund et al. |
| 9,839,764 B2 | 12/2017 | Chouinard |
| 9,848,882 B2 | 12/2017 | Lippert |
| D809,138 S | 1/2018 | Khan et al. |
| 9,950,137 B2 | 4/2018 | Lippert et al. |
| 9,999,748 B2 | 6/2018 | Cajamarca et al. |
| 10,016,210 B2 | 7/2018 | Lenker et al. |
| 10,028,666 B2 | 7/2018 | Gregorich |
| 10,052,013 B2 | 8/2018 | Boulais |
| 10,149,608 B2 | 12/2018 | Fujitani |
| D839,426 S | 1/2019 | Bajwa |
| D847,335 S | 4/2019 | Kuwada |
| 10,252,024 B2 | 4/2019 | Northrop |
| D855,180 S | 7/2019 | Haefliger |
| 10,350,383 B2 | 7/2019 | Shuman |
| 10,363,389 B2 | 7/2019 | Lippert et al. |
| D855,800 S | 8/2019 | Gabay et al. |
| 10,420,537 B2 | 9/2019 | Salahieh et al. |
| 10,441,746 B2 | 10/2019 | Besselink |
| 10,456,556 B2 | 10/2019 | Cabiri |
| 10,639,456 B2 | 5/2020 | Peralta |
| 10,675,057 B2 | 6/2020 | Krieger et al. |
| 10,675,444 B2 | 6/2020 | Kauphusman et al. |
| 10,758,710 B2 | 9/2020 | Romano |
| 10,806,893 B2 | 10/2020 | Jaroch |
| 10,821,268 B2 | 11/2020 | Snyder et al. |
| 10,835,183 B2 | 11/2020 | Sham et al. |
| 11,007,345 B2 | 5/2021 | Cottone |
| 11,052,226 B2 | 7/2021 | Salahieh et al. |
| 11,052,228 B2 | 7/2021 | Lippert et al. |
| 11,141,566 B2 | 10/2021 | Cabiri |
| D946,148 S | 3/2022 | Takemoto |
| 11,278,704 B2 | 3/2022 | Pleijers |
| 11,305,095 B2 | 4/2022 | Snyder et al. |
| 11,317,938 B2 | 5/2022 | Lenker et al. |
| 11,369,351 B2 | 6/2022 | Davis et al. |
| 11,471,645 B2 | 10/2022 | McNiven et al. |
| 11,497,512 B2 | 11/2022 | Wallace et al. |
| 11,565,093 B2 | 1/2023 | Kirt et al. |
| D980,427 S | 3/2023 | Method et al. |
| 11,679,236 B2 | 6/2023 | Von et al. |
| 11,724,065 B2 | 8/2023 | Tilson et al. |
| 11,724,068 B2 | 8/2023 | Von et al. |
| 11,759,217 B2 | 9/2023 | Keating et al. |
| 11,766,539 B2 | 9/2023 | Yee et al. |
| D1,014,751 S | 2/2024 | Shih |
| 11,918,753 B2 | 3/2024 | Moquin et al. |
| 11,957,312 B2 | 4/2024 | Boulais |
| 2001/0009980 A1 | 7/2001 | Richardson et al. |
| 2001/0044624 A1 | 11/2001 | Seraj et al. |
| 2002/0013540 A1 | 1/2002 | Jacobsen et al. |
| 2002/0019599 A1 | 2/2002 | Rooney et al. |
| 2002/0049392 A1 | 4/2002 | Demello |
| 2002/0062524 A1 | 5/2002 | Vogland et al. |
| 2002/0068912 A1 | 6/2002 | Merdan |
| 2002/0078808 A1 | 6/2002 | Jacobsen et al. |
| 2002/0082524 A1 | 6/2002 | Anderson et al. |
| 2003/0009208 A1 | 1/2003 | Snyder et al. |
| 2003/0023190 A1 | 1/2003 | Cox |
| 2003/0060732 A1 | 3/2003 | Jacobsen et al. |
| 2003/0069521 A1 | 4/2003 | Reynolds et al. |
| 2003/0069522 A1 | 4/2003 | Jacobsen et al. |
| 2003/0093059 A1 | 5/2003 | Griffin et al. |
| 2003/0125641 A1 | 7/2003 | Jafari et al. |
| 2004/0039371 A1 | 2/2004 | Tockman et al. |
| 2004/0054349 A1 | 3/2004 | Brightbill |
| 2004/0087933 A1 | 5/2004 | Lee et al. |
| 2004/0093060 A1 | 5/2004 | Seguin et al. |
| 2004/0102719 A1 | 5/2004 | Keith et al. |
| 2004/0102720 A1 | 5/2004 | Kellerman et al. |
| 2004/0111044 A1 | 6/2004 | Davis et al. |
| 2004/0122340 A1 | 6/2004 | Vrba et al. |
| 2004/0167437 A1 | 8/2004 | Sharrow et al. |
| 2004/0167440 A1 | 8/2004 | Sharrow |

(56) References Cited

U.S. PATENT DOCUMENTS

| | | |
|---|---|---|
| 2004/0167443 A1 | 8/2004 | Shireman et al. |
| 2004/0171996 A1 | 9/2004 | Kiemeneij |
| 2004/0181174 A2 | 9/2004 | Davis et al. |
| 2004/0186485 A1 | 9/2004 | Kear |
| 2004/0193140 A1 | 9/2004 | Griffin et al. |
| 2004/0225292 A1 | 11/2004 | Sasso et al. |
| 2004/0254450 A1 | 12/2004 | Griffin et al. |
| 2005/0054953 A1 | 3/2005 | Ryan et al. |
| 2005/0065456 A1 | 3/2005 | Eskuri |
| 2005/0124976 A1 | 6/2005 | Devens et al. |
| 2005/0137501 A1 | 6/2005 | Euteneuer et al. |
| 2005/0216049 A1 | 9/2005 | Jones et al. |
| 2005/0274384 A1 | 12/2005 | Tran et al. |
| 2006/0006649 A1 | 1/2006 | Galdonik et al. |
| 2006/0041186 A1 | 2/2006 | Vancaillie |
| 2006/0074442 A1 | 4/2006 | Noriega et al. |
| 2006/0089618 A1 | 4/2006 | McFerran et al. |
| 2006/0112802 A1 | 6/2006 | Fujinami |
| 2006/0121218 A1 | 6/2006 | Obara et al. |
| 2006/0189896 A1 | 8/2006 | Davis et al. |
| 2006/0241519 A1 | 10/2006 | Hojeibane et al. |
| 2006/0247661 A1 | 11/2006 | Richards et al. |
| 2006/0262474 A1 | 11/2006 | Chen et al. |
| 2007/0010786 A1 | 1/2007 | Casey et al. |
| 2007/0055302 A1 | 3/2007 | Henry et al. |
| 2007/0100285 A1 | 5/2007 | Griffin et al. |
| 2007/0112331 A1 | 5/2007 | Weber et al. |
| 2007/0135763 A1 | 6/2007 | Musbach et al. |
| 2007/0142893 A1 | 6/2007 | Buiser et al. |
| 2007/0167876 A1 | 7/2007 | Euteneuer et al. |
| 2007/0185415 A1 | 8/2007 | Ressemann et al. |
| 2007/0208405 A1 | 9/2007 | Goodin et al. |
| 2007/0213689 A1 | 9/2007 | Grewe et al. |
| 2007/0221230 A1 | 9/2007 | Thompson et al. |
| 2007/0233039 A1 | 10/2007 | Mitelberg |
| 2007/0250036 A1 | 10/2007 | Volk et al. |
| 2007/0282270 A1 | 12/2007 | Mathews et al. |
| 2007/0287955 A1 | 12/2007 | Layman et al. |
| 2008/0021347 A1 | 1/2008 | Jacobsen et al. |
| 2008/0021401 A1 | 1/2008 | Jacobsen et al. |
| 2008/0021404 A1* | 1/2008 | Jacobsen ........... A61M 25/0013 604/164.13 |
| 2008/0021406 A1 | 1/2008 | Jacobsen et al. |
| 2008/0033421 A1 | 2/2008 | Davis et al. |
| 2008/0064989 A1 | 3/2008 | Chen et al. |
| 2008/0077049 A1 | 3/2008 | Hirshman |
| 2008/0086854 A1 | 4/2008 | Boyd et al. |
| 2008/0097246 A1 | 4/2008 | Stafford |
| 2008/0097247 A1 | 4/2008 | Eskuri |
| 2008/0097248 A1 | 4/2008 | Munoz et al. |
| 2008/0114303 A1 | 5/2008 | Tremaglio |
| 2008/0119869 A1 | 5/2008 | Teague et al. |
| 2008/0122226 A1 | 5/2008 | Madison |
| 2008/0125674 A1 | 5/2008 | Bilecen et al. |
| 2008/0140101 A1 | 6/2008 | Carley et al. |
| 2008/0147170 A1 | 6/2008 | Vrba |
| 2008/0188298 A1 | 8/2008 | Seelig et al. |
| 2008/0188928 A1 | 8/2008 | Salahieh et al. |
| 2008/0200839 A1 | 8/2008 | Bunch et al. |
| 2008/0262474 A1 | 10/2008 | Northrop |
| 2008/0269641 A1 | 10/2008 | O'Shaughnessy et al. |
| 2008/0319525 A1 | 12/2008 | Tieu et al. |
| 2009/0036832 A1 | 2/2009 | Skujins et al. |
| 2009/0036833 A1 | 2/2009 | Parins |
| 2009/0043283 A1 | 2/2009 | Turnlund et al. |
| 2009/0043372 A1 | 2/2009 | Northrop et al. |
| 2009/0043483 A1 | 2/2009 | Abe et al. |
| 2009/0118675 A1 | 5/2009 | Czyscon et al. |
| 2009/0118704 A1 | 5/2009 | Sharrow et al. |
| 2009/0163945 A1 | 6/2009 | Richard et al. |
| 2009/0177119 A1 | 7/2009 | Heidner et al. |
| 2009/0177185 A1 | 7/2009 | Northrop |
| 2009/0254000 A1 | 10/2009 | Layman et al. |
| 2009/0292225 A1 | 11/2009 | Chen et al. |
| 2009/0318892 A1 | 12/2009 | Aboytes et al. |
| 2010/0063479 A1 | 3/2010 | Merdan et al. |
| 2010/0069882 A1 | 3/2010 | Jennings et al. |
| 2010/0114017 A1 | 5/2010 | Lenker et al. |
| 2010/0114302 A1 | 5/2010 | Tzafriri et al. |
| 2010/0139465 A1 | 6/2010 | Christian et al. |
| 2010/0145308 A1 | 6/2010 | Layman et al. |
| 2010/0228150 A1 | 9/2010 | Zimmerman et al. |
| 2010/0256527 A1 | 10/2010 | Lippert et al. |
| 2010/0256528 A1 | 10/2010 | Lippert et al. |
| 2010/0256601 A1 | 10/2010 | Lippert et al. |
| 2010/0256602 A1 | 10/2010 | Lippert et al. |
| 2010/0256603 A1 | 10/2010 | Lippert et al. |
| 2010/0256604 A1 | 10/2010 | Lippert et al. |
| 2010/0256605 A1 | 10/2010 | Lippert et al. |
| 2010/0256606 A1 | 10/2010 | Lippert et al. |
| 2010/0318066 A1 | 12/2010 | Miyata et al. |
| 2011/0011226 A1 | 1/2011 | Tsurusawa et al. |
| 2011/0022003 A1 | 1/2011 | Tekulve |
| 2011/0160680 A1 | 6/2011 | Cage et al. |
| 2011/0245807 A1 | 10/2011 | Sakata et al. |
| 2011/0245808 A1 | 10/2011 | Voeller et al. |
| 2011/0251519 A1 | 10/2011 | Romoscanu |
| 2011/0313417 A1 | 12/2011 | De et al. |
| 2012/0046575 A1 | 2/2012 | Brown |
| 2012/0065623 A1 | 3/2012 | Nelson et al. |
| 2012/0158034 A1 | 6/2012 | Wilson et al. |
| 2012/0209073 A1 | 8/2012 | McWeeney et al. |
| 2012/0239074 A1 | 9/2012 | Aboytes et al. |
| 2012/0271397 A1 | 10/2012 | Muzslay et al. |
| 2012/0289938 A1 | 11/2012 | Northrop et al. |
| 2013/0018280 A1 | 1/2013 | Tano et al. |
| 2013/0018359 A1 | 1/2013 | Coyle |
| 2013/0096553 A1 | 4/2013 | Hill et al. |
| 2013/0110000 A1 | 5/2013 | Tully et al. |
| 2013/0131642 A1 | 5/2013 | Miyata et al. |
| 2013/0144267 A1 | 6/2013 | Chan et al. |
| 2013/0184703 A1 | 7/2013 | Shireman et al. |
| 2013/0226033 A1 | 8/2013 | Eskuri |
| 2013/0255456 A1 | 10/2013 | Christian et al. |
| 2013/0274784 A1 | 10/2013 | Lenker et al. |
| 2014/0012281 A1 | 1/2014 | Wang et al. |
| 2014/0031719 A1 | 1/2014 | Kanazawa |
| 2014/0058324 A1 | 2/2014 | Salahieh et al. |
| 2014/0094787 A1 | 4/2014 | Reynolds |
| 2014/0187983 A1 | 7/2014 | Anderson |
| 2014/0257363 A1 | 9/2014 | Lippert |
| 2014/0276109 A1 | 9/2014 | Gregorich |
| 2014/0276117 A1 | 9/2014 | Burkett |
| 2014/0276787 A1 | 9/2014 | Wang et al. |
| 2014/0279109 A1 | 9/2014 | Vasquez et al. |
| 2014/0309657 A1 | 10/2014 | Ben-Ami |
| 2014/0336620 A1 | 11/2014 | Layman et al. |
| 2014/0343538 A1 | 11/2014 | Lenker et al. |
| 2015/0011834 A1 | 1/2015 | Ayala et al. |
| 2015/0011964 A1 | 1/2015 | Abner et al. |
| 2015/0057639 A1 | 2/2015 | Storbeck et al. |
| 2015/0190614 A1 | 7/2015 | Uihlein |
| 2015/0190615 A1 | 7/2015 | Shaltis |
| 2015/0216533 A1 | 8/2015 | Gray et al. |
| 2015/0238734 A1 | 8/2015 | Kanazawa |
| 2015/0290432 A1 | 10/2015 | Mathews et al. |
| 2015/0297863 A1 | 10/2015 | Hannon et al. |
| 2015/0305710 A1 | 10/2015 | Stigall et al. |
| 2015/0306355 A1 | 10/2015 | Idstrom |
| 2016/0001048 A1 | 1/2016 | Koike |
| 2016/0008585 A1 | 1/2016 | Tano |
| 2016/0045101 A1 | 2/2016 | Nakatate et al. |
| 2016/0058382 A1 | 3/2016 | Burkett et al. |
| 2016/0089128 A1 | 3/2016 | Weber et al. |
| 2016/0113793 A1 | 4/2016 | Nishigishi |
| 2016/0135827 A1 | 5/2016 | Elsesser et al. |
| 2016/0199620 A1 | 7/2016 | Pokorney et al. |
| 2016/0235337 A1 | 8/2016 | Govari et al. |
| 2016/0287054 A1 | 10/2016 | Fujitani |
| 2016/0310702 A1 | 10/2016 | Cabiri |
| 2016/0361520 A1 | 12/2016 | Braun |
| 2016/0367788 A1 | 12/2016 | Jimenez et al. |
| 2016/0375226 A1 | 12/2016 | Nabeshima et al. |
| 2017/0047740 A1 | 2/2017 | Narla |

(56) References Cited

U.S. PATENT DOCUMENTS

| | | | |
|---|---|---|---|
| 2017/0049594 A1 | 2/2017 | Banas et al. |
| 2017/0136213 A1 | 5/2017 | Kauphusman et al. |
| 2017/0189643 A1 | 7/2017 | Christian et al. |
| 2017/0203076 A1 | 7/2017 | Groneberg et al. |
| 2017/0215954 A1 | 8/2017 | Datta et al. |
| 2017/0234411 A1 | 8/2017 | Dewaele et al. |
| 2017/0281909 A1 | 10/2017 | Northrop et al. |
| 2018/0015260 A1 | 1/2018 | Sano et al. |
| 2018/0015261 A1 | 1/2018 | Lippert et al. |
| 2018/0015262 A1 | 1/2018 | Lippert et al. |
| 2018/0015263 A1 | 1/2018 | Lippert et al. |
| 2018/0028177 A1 | 2/2018 | Van et al. |
| 2018/0071496 A1 | 3/2018 | Snyder et al. |
| 2018/0177517 A1 | 6/2018 | Lippert et al. |
| 2018/0185619 A1 | 7/2018 | Batman et al. |
| 2018/0193603 A1 | 7/2018 | Falb et al. |
| 2018/0193607 A1 | 7/2018 | Lippert et al. |
| 2018/0207407 A1 | 7/2018 | Tanigaki |
| 2019/0008639 A1 | 1/2019 | Landon et al. |
| 2019/0105463 A1 | 4/2019 | Christian et al. |
| 2019/0175869 A1 | 6/2019 | Kirt et al. |
| 2019/0255290 A1 | 8/2019 | Snyder et al. |
| 2019/0290883 A1 | 9/2019 | Lippert et al. |
| 2019/0358434 A1 | 11/2019 | Fuller et al. |
| 2020/0016378 A1 | 1/2020 | Williams et al. |
| 2020/0054860 A1 | 2/2020 | McElhaney et al. |
| 2020/0094027 A1 | 3/2020 | Davis |
| 2020/0121308 A1 | 4/2020 | Davis et al. |
| 2020/0222666 A1 | 7/2020 | Chan et al. |
| 2020/0222672 A1 | 7/2020 | Davis et al. |
| 2020/0330734 A1 | 10/2020 | Sugita et al. |
| 2020/0345975 A1 | 11/2020 | Snyder |
| 2021/0008351 A1 | 1/2021 | Snyder et al. |
| 2021/0022748 A1 | 1/2021 | Lorenzo |
| 2021/0162184 A1 | 6/2021 | Lippert et al. |
| 2021/0178128 A1 | 6/2021 | Lippert et al. |
| 2021/0213241 A1 | 7/2021 | Christian et al. |
| 2021/0228845 A1 | 7/2021 | Lippert et al. |
| 2021/0283372 A1 | 9/2021 | Murphy |
| 2021/0283380 A1 | 9/2021 | Lippert et al. |
| 2021/0307766 A1 | 10/2021 | Keating et al. |
| 2021/0346656 A1 | 11/2021 | Lippert et al. |
| 2022/0039644 A1 | 2/2022 | Dayton et al. |
| 2022/0047845 A1 | 2/2022 | Niederhauser et al. |
| 2022/0105312 A1 | 4/2022 | Davis |
| 2022/0105318 A1 | 4/2022 | Davis et al. |
| 2022/0118225 A1 | 4/2022 | Snyder et al. |
| 2022/0176075 A1 | 6/2022 | McDermott et al. |
| 2022/0218358 A1 | 7/2022 | Dagan et al. |
| 2022/0273474 A1 | 9/2022 | Koop et al. |
| 2022/0296850 A1 | 9/2022 | Lippert |
| 2022/0323166 A1 | 10/2022 | Tilson et al. |
| 2022/0378459 A1 | 12/2022 | Lippert |
| 2023/0010697 A1 | 1/2023 | Sharma et al. |
| 2023/0069698 A1 | 3/2023 | Hallauer et al. |
| 2023/0071512 A1 | 3/2023 | Maggio et al. |
| 2023/0082226 A1 | 3/2023 | Lippert et al. |
| 2023/0285720 A1 | 9/2023 | Isogai |
| 2023/0405276 A1 | 12/2023 | Cabiri |
| 2024/0123196 A1 | 4/2024 | Lippert et al. |
| 2024/0198059 A1 | 6/2024 | Lippert et al. |
| 2024/0299710 A1 | 9/2024 | Davis et al. |

FOREIGN PATENT DOCUMENTS

| | | |
|---|---|---|
| AU | 07745/59 B2 | 7/2004 |
| AU | 2008229892 A1 | 10/2008 |
| BR | 9709363 A | 1/2000 |
| BR | 9712829 A | 1/2000 |
| CA | 2255781 A1 | 11/1997 |
| CA | 2266685 A1 | 3/1998 |
| CA | 2395149 A1 | 6/2001 |
| CN | 1225282 A | 8/1999 |
| CN | 1230914 A | 10/1999 |
| CN | 1324285 A | 11/2001 |
| CN | 1422673 A | 6/2003 |
| CN | 1518428 A | 8/2004 |
| CN | 1781684 A | 6/2006 |
| CN | 1897892 A | 1/2007 |
| CN | 101001660 A | 7/2007 |
| CN | 101209365 A | 7/2008 |
| CN | 101304778 A | 11/2008 |
| CN | 201239164 Y | 5/2009 |
| CN | 101815553 A | 8/2010 |
| CN | 102049085 A | 5/2011 |
| CN | 102107041 A | 6/2011 |
| CN | 102438691 A | 5/2012 |
| CN | 102548603 A | 7/2012 |
| CN | 102639303 A | 8/2012 |
| CN | 102824681 A | 12/2012 |
| CN | 102847225 A | 1/2013 |
| CN | 103301553 A | 9/2013 |
| CN | 103566457 A | 2/2014 |
| CN | 103764012 A | 4/2014 |
| CN | 103799980 A | 5/2014 |
| CN | 103860265 A | 6/2014 |
| CN | 104271035 A | 1/2015 |
| CN | 104302345 A | 1/2015 |
| CN | 104427950 A | 3/2015 |
| CN | 104602616 A | 5/2015 |
| CN | 104602718 A | 5/2015 |
| CN | 104619247 A | 5/2015 |
| CN | 104759022 A | 7/2015 |
| CN | 104812420 A | 7/2015 |
| CN | 105209102 A | 12/2015 |
| CN | 105228536 A | 1/2016 |
| CN | 105361918 A | 3/2016 |
| CN | 105545375 A | 5/2016 |
| CN | 105582611 A | 5/2016 |
| CN | 105682725 A | 6/2016 |
| CN | 105682729 A | 6/2016 |
| CN | 105828690 A | 8/2016 |
| CN | 105979880 A | 9/2016 |
| CN | 107206216 A | 9/2017 |
| CN | 109125889 A | 1/2019 |
| CN | 109715245 A | 5/2019 |
| CN | 109789296 A | 5/2019 |
| DE | 60036882 T2 | 7/2008 |
| DE | 69738235 T2 | 7/2008 |
| EP | 0521595 A2 | 1/1993 |
| EP | 0921754 A1 | 6/1999 |
| EP | 0998323 A1 | 5/2000 |
| EP | 0934141 B1 | 11/2005 |
| EP | 1239901 B1 | 10/2007 |
| EP | 1844911 A1 | 10/2007 |
| EP | 1940498 A1 | 7/2008 |
| EP | 2964305 A2 | 1/2016 |
| EP | 2414022 B1 | 8/2017 |
| EP | 3866902 A1 | 8/2021 |
| ES | 2293660 T3 | 3/2008 |
| GB | 2478988 A | 9/2011 |
| JP | 59-102509 A | 6/1984 |
| JP | 06-154335 A | 6/1994 |
| JP | 07-008560 A | 1/1995 |
| JP | 08-215313 A | 8/1996 |
| JP | 08-243168 A | 9/1996 |
| JP | 08-243169 A | 9/1996 |
| JP | 08-308934 A | 11/1996 |
| JP | 09-288239 A | 11/1997 |
| JP | 11-294497 A | 10/1999 |
| JP | 2000-503225 A | 3/2000 |
| JP | 2000-116787 A | 4/2000 |
| JP | 2000-126301 A | 5/2000 |
| JP | 2000-511094 A | 8/2000 |
| JP | 2000-343313 A | 12/2000 |
| JP | 2001-500808 A | 1/2001 |
| JP | 2002-543896 A | 12/2002 |
| JP | 2003-011117 A | 1/2003 |
| JP | 2004-025340 A | 1/2004 |
| JP | 2004-136121 A | 5/2004 |
| JP | 2004-329552 A | 11/2004 |
| JP | 2004-535233 A | 11/2004 |
| JP | 2005-514115 A | 5/2005 |
| JP | 2005-533594 A | 11/2005 |

(56) References Cited

FOREIGN PATENT DOCUMENTS

| | | |
|---|---|---|
| JP | 2005-534407 A | 11/2005 |
| JP | 2007-514458 A | 6/2007 |
| JP | 2007-313638 A | 12/2007 |
| JP | 2008-178656 A | 8/2008 |
| JP | 2008-536639 A | 9/2008 |
| JP | 2010-029736 A | 2/2010 |
| JP | 2010-503484 A | 2/2010 |
| JP | 2010-535583 A | 11/2010 |
| JP | 2010-535588 A | 11/2010 |
| JP | 2011-206175 A | 10/2011 |
| JP | 4805208 B2 | 11/2011 |
| JP | 4845313 B2 | 12/2011 |
| JP | 2012-502743 A | 2/2012 |
| JP | 2012-522607 A | 9/2012 |
| JP | 2013-106854 A | 6/2013 |
| JP | 2013-523282 A | 6/2013 |
| JP | 2013-176560 A | 9/2013 |
| JP | 2014-023727 A | 2/2014 |
| JP | 2015-073861 A | 4/2015 |
| JP | 2015-181723 A | 10/2015 |
| JP | 2015-186427 A | 10/2015 |
| JP | 2016-013269 A | 1/2016 |
| JP | 2017-169253 A | 9/2017 |
| KR | 2000-0015896 A | 3/2000 |
| KR | 10-2000-0036139 A | 6/2000 |
| NL | 2017570 B1 | 4/2018 |
| RU | 91674 U1 | 2/2010 |
| TW | 412468 B | 11/2000 |
| WO | 94/06503 A1 | 3/1994 |
| WO | 94/19039 A1 | 9/1994 |
| WO | 95/24237 A2 | 9/1995 |
| WO | 97/25914 A1 | 7/1997 |
| WO | 97/43949 A1 | 11/1997 |
| WO | 98/55173 A1 | 12/1998 |
| WO | 98/58697 A1 | 12/1998 |
| WO | 99/04847 A1 | 2/1999 |
| WO | 99/53824 A2 | 10/1999 |
| WO | 2004/011076 A2 | 2/2004 |
| WO | 2006/025931 A1 | 3/2006 |
| WO | 2006/058234 A2 | 6/2006 |
| WO | 2006/113863 A2 | 10/2006 |
| WO | 2007/050718 A1 | 5/2007 |
| WO | 2008/034010 A2 | 3/2008 |
| WO | 2009/020691 A2 | 2/2009 |
| WO | 2009/020836 A1 | 2/2009 |
| WO | 2009/020961 A1 | 2/2009 |
| WO | 2009/020962 A1 | 2/2009 |
| WO | 2009/058705 A2 | 5/2009 |
| WO | 2009/143160 A1 | 11/2009 |
| WO | 2010/077692 A2 | 7/2010 |
| WO | 2010/115163 A1 | 10/2010 |
| WO | 2011/123689 A1 | 10/2011 |
| WO | 2014/005095 A1 | 1/2014 |
| WO | 2014/066104 A1 | 5/2014 |
| WO | 2014/077881 A1 | 5/2014 |
| WO | 2014/138580 A2 | 9/2014 |
| WO | 2016/047499 A1 | 3/2016 |
| WO | 2016/117238 A1 | 7/2016 |
| WO | 2016/136609 A1 | 9/2016 |
| WO | 2016/152194 A1 | 9/2016 |
| WO | 2016/158671 A1 | 10/2016 |
| WO | 2017/151292 A1 | 9/2017 |
| WO | 2018/017349 A1 | 1/2018 |
| WO | 2018/017351 A1 | 1/2018 |
| WO | 2018/052815 A1 | 3/2018 |
| WO | 2018/218216 | 11/2018 |
| WO | 2020/217171 A1 | 10/2020 |
| WO | 2021/150920 A1 | 7/2021 |
| WO | 2022/159139 A1 | 7/2022 |

OTHER PUBLICATIONS

Final Office Action received for U.S. Appl. No. 16/855,366, mailed on Dec. 8, 2022, 18 pages.
Final Office Action received for U.S. Appl. No. 16/616,220, mailed on Oct. 12, 2022, 17 pages.
Final Office Action received for U.S. Appl. No. 16/742,211, mailed on Mar. 14, 2023, 22 pages.
Non-Final Office Action received for U.S. Appl. No. 16/742,211, mailed on Aug. 15, 2022, 20 pages.
Non-Final Office Action received for U.S. Appl. No. 16/855,366, mailed on Jul. 11, 2022, 13 pages.
Non-Final Office Action received for U.S. Appl. No. 17/036,302, mailed on Mar. 1, 2023, 29 pages.
Non-Final Office Action received for U.S. Appl. No. 17/177,782, mailed on Jan. 23, 2023, 14 pages.
Non-Final Office Action received for U.S. Appl. No. 17/177,782, mailed on Nov. 4, 2022, 7 pages.
Penumbra Augments Vascular Franchise with Latest Indigo System Launch and Expands Medical/Scientific Leadership, Jul. 14, 2020, https://investors.penumbrainc.com/investors-relations/press-releases/press-release-details/2020/Penumbra-Augments-Vascular-Franchise-with-Latest-Indigo-System-Launch-and-Expands-MedicalScientific-Leadership/default.aspx.
Strength of Materials/Torsion, Wikibooks, 3 pp., accessed Feb. 22, 2023 (en.wikibooks.org/wiki/Strength_of_Materials/Torsion) (last edited Feb. 1, 2022) (Year: 2022).
Non-Final Office Action received for U.S. Appl. No. 15/611,328, mailed on Jun. 29, 2020, 13 pages.
Non-Final Office Action received for U.S. Appl. No. 15/848,878, mailed on Jun. 3, 2021, 13 pages.
Non-Final Office Action received for U.S. Appl. No. 15/917,255, mailed on Aug. 17, 2020, 12 pages.
Non-Final Office Action received for U.S. Appl. No. 16/281,046, mailed on Oct. 29, 2020, 18 pages.
Non-Final Office Action received for U.S. Appl. No. 16/616,139, mailed on Oct. 26, 2021, 11 pages.
Non-Final Office Action received for U.S. Appl. No. 16/616,220, mailed on Jun. 3, 2022, 20 pages.
Non-Final Office Action received for U.S. Appl. No. 16/855,366, mailed on Jun. 23, 2021, 15 pages.
Notice of Allowance received for U.S. Appl. No. 16/212,425, mailed on Dec. 23, 2020, 12 pages.
Notice of Allowance received for U.S. Appl. No. 16/212,425, mailed on Jan. 25, 2021, 2 pages.
Office Action received for U.S. Appl. No. 12/633,727, mailed on Oct. 16, 2012.
Office Action received for U.S. Appl. No. 12/753,831, mailed on Feb. 1, 2012.
Office Action received for U.S. Appl. No. 12/753,831, mailed on Mar. 21, 2014.
Office Action received for U.S. Appl. No. 12/753,836, mailed on Dec. 9, 2011.
Office Action received for U.S. Appl. No. 12/753,836, mailed on Dec. 23, 2016.
Office Action received for U.S. Appl. No. 12/753,836, mailed on Jul. 31, 2014.
Office Action received for U.S. Appl. No. 12/753,836, mailed on Jun. 26, 2015.
Office Action received for U.S. Appl. No. 12/753,839, mailed on Feb. 7, 2012.
Office Action received for U.S. Appl. No. 12/753,839, mailed on May 5, 2014.
Office Action received for U.S. Appl. No. 12/753,842, mailed on Aug. 1, 2012.
Office Action received for U.S. Appl. No. 12/753,842, mailed on Jan. 29, 2014.
Office Action received for U.S. Appl. No. 12/753,849, mailed on Jan. 3, 2013.
Office Action received for U.S. Appl. No. 12/753,849, mailed on May 10, 2011.
Office Action received for U.S. Appl. No. 12/753,849, mailed on May 27, 2014.
Office Action received for U.S. Appl. No. 12/753,849, mailed on Oct. 18, 2011.
Office Action received for U.S. Appl. No. 12/753,855, mailed on Feb. 28, 2014.

(56) References Cited

OTHER PUBLICATIONS

Office Action received for U.S. Appl. No. 12/753,855, mailed on May 21, 2015.
Office Action received for U.S. Appl. No. 12/753,855, mailed on Sep. 15, 2011.
Office Action received for U.S. Appl. No. 12/753,858, mailed on Dec. 30, 2015.
Office Action received for U.S. Appl. No. 12/753,858, mailed on Feb. 3, 2012.
Office Action received for U.S. Appl. No. 12/753,858, mailed on Mar. 13, 2018.
Office Action received for U.S. Appl. No. 12/753,858, mailed on Mar. 27, 2017.
Office Action received for U.S. Appl. No. 12/753,858, mailed on Mar. 29, 2013.
Office Action received for U.S. Appl. No. 12/753,858, mailed on May 10, 2011.
Office Action received for U.S. Appl. No. 12/753,858, mailed on Oct. 24, 2016.
Office Action received for U.S. Appl. No. 12/753,858, mailed on Sep. 4, 2014.
Office Action received for U.S. Appl. No. 13/901,375, mailed on Dec. 10, 2015.
Office Action received for U.S. Appl. No. 15/465,399, mailed on Apr. 23, 2018.
Office Action received for U.S. Appl. No. 15/606,607, mailed on May 14, 2019.
Office Action received for U.S. Appl. No. 15/611,344, mailed on Mar. 26, 2019.
Office Action received for U.S. Appl. No. 15/611,344, mailed on May 21, 2020.
Office Action received for U.S. Appl. No. 15/848,878, mailed on Feb. 5, 2020.
Office Action received for U.S. Appl. No. 15/848,878, mailed on Oct. 29, 2019.
Office Action received for U.S. Appl. No. 16/212,425, mailed on Mar. 16, 2020.
Office Action received for U.S. Appl. No. 12/753,855 mailed on May 5, 2016.
Office Action received for U.S. Appl. No. 13/901,375, mailed on Aug. 1, 2016.
U.S. Appl. No. 16/281,046, filed Feb. 20, 2019 by Snyder.
U.S. Appl. No. 16/742,211, filed Jan. 14, 2020, by Clark C. Davis et al.
U.S. Appl. No. 16/439,894, filed Jun. 13, 2019, by Lippert.
U.S. Appl. No. 15/917,255, filed Mar. 9, 2018, by Lippert.
Final Office Action received for U.S. Appl. No. 16/855,366, mailed on Jun. 20, 2024, 17 pages.
Final Office Action received for U.S. Appl. No. 17/836,863, mailed on Jun. 25, 2024, 6 pages.
Non-Final Office Action received for U.S. Appl. No. 17/382,271, mailed on May 14, 2024, 22 pages.
Non-Final Office Action received for U.S. Appl. No. 17/493,265, mailed on Jun. 11, 2024, 19 pages.
Chinese Search Report for Chinese Application No. 201780070242.X, dated Sep. 14, 2016, 4 pages.
International Search Report and Written Opinion received for PCT Patent Application No. PCT/US22/42514, mailed on Dec. 28, 2022, 11 pages.
International Search Report and Written Opinion received for PCT Patent Application No. PCT/US22/42517, mailed on Feb. 7, 2023, 11 pages.
International Search Report and Written Opinion received for PCT Patent Application No. PCT/US2021/053647, mailed on Dec. 28, 2021, 9 pages.
International Search Report and Written Opinion received for PCT Patent Application No. PCT/US2021/053652, mailed on Dec. 28, 2021, 9 pages.
InternationalSearch Report and Written Opinion for application PCT/US2017/050802 mailed on Nov. 7, 2017.
Final Office Action received for U.S. Appl. No. 12/753,831, mailed on May 31, 2012.
Final Office Action received for U.S. Appl. No. 12/753,836 mailed on Feb. 17, 2016.
Final Office Action received for U.S. Appl. No. 16/212,425, mailed on Aug. 3, 2020, 14 pages.
Final Office Action received for U.S. Appl. No. 12/753,831, mailed on Aug. 29, 2014.
Final Office Action received for U.S. Appl. No. 12/753,836, mailed on Jan. 9, 2015.
Final Office Action received for U.S. Appl. No. 12/753,836, mailed on Jul. 14, 2017.
Final Office Action received for U.S. Appl. No. 12/753,836, mailed on May 1, 2012.
Final Office Action received for U.S. Appl. No. 12/753,839, mailed on May 31, 2012.
Final Office Action received for U.S. Appl. No. 12/753,842, mailed on Jan. 9, 2013.
Final Office Action received for U.S. Appl. No. 12/753,842, mailed on Sep. 4, 2014.
Final Office Action received for U.S. Appl. No. 12/753,849, mailed on Jun. 6, 2012.
Final Office Action received for U.S. Appl. No. 12/753,849, mailed on Oct. 9, 2013.
Final Office Action received for U.S. Appl. No. 12/753,855, mailed on Apr. 18, 2012.
Final Office Action received for U.S. Appl. No. 12/753,855, mailed on Jan. 13, 2015.
Final Office Action received for U.S. Appl. No. 12/753,858, mailed on Jan. 17, 2014.
Final Office Action received for U.S. Appl. No. 12/753,858, mailed on Jul. 18, 2012.
Final Office Action received for U.S. Appl. No. 12/753,858, mailed on May 28, 2015.
Final Office Action received for U.S. Appl. No. 12/753,858, mailed on Nov. 14, 2018.
Final Office Action received for U.S. Appl. No. 12/753,858, mailed on Oct. 19, 2011.
Final Office Action received for U.S. Appl. No. 12/753,858, mailed on Oct. 20, 2017.
Final Office Action received for U.S. Appl. No. 15/606,607, mailed on Nov. 19, 2019.
Final Office Action received for U.S. Appl. No. 15/611,344, mailed on Nov. 12, 2019.
Final Office Action received for U.S. Appl. No. 15/848,878, mailed on Aug. 27, 2020, 13 pages.
Final Office Action received for U.S. Appl. No. 15/848,878, mailed on Sep. 22, 2021, 12 pages.
Final Office Action received for U.S. Appl. No. 16/281,046, mailed on May 11, 2021, 18 pages.
Final Office Action received for U.S. Appl. No. 17/216,127, mailed on Jun. 13, 2022, 8 pages.
Final Office Action received for U.S. Appl. No. 14/199,675, mailed on May 18, 2017.
Final Office Action received for U.S. Appl. No. 15/611,328, mailed on Sep. 24, 2019.
Final Office Action received for U.S. Appl. No. 15/698,553, mailed on Nov. 27, 2019.
Final Rejection received for U.S. Appl. No. 15/606,607, mailed on Dec. 15, 2020, 24 pages.
International Search Report and Written Opinion for application No. PCT/US17/41305 dated Oct. 2, 2017.
International Search Report and Written Opinion for Application PCT/US2017/050602 mailed on Nov. 7, 2017.
International Search Report and Written Opinion for PCT/US2009/067217 dated Dec. 16, 2010.
International Search Report and Written Opinion for PCT/US2010/029867 dated Jun. 1, 2010.
International Search Report and Written Opinion for PCT/US2014/021742 dated Aug. 27, 2014.
International Search Report and Written Opinion for PCT/US2017/041299 mailed on Oct. 2, 2017.

(56) References Cited

OTHER PUBLICATIONS

International Search Report and Written Opinion for PCT/US2017/041301 mailed on Oct. 2, 2017.
International Search Report and Written Opinion for PCT/US2017/068056 mailed on Feb. 26, 2018.
International Search Report and Written Opinion for PCT/US2018/034756 mailed on Aug. 14, 2018.
International Search Report and Written Opinion for PCT/US2019/019046, mailed on May 17, 2019.
International Search Report and Written Opinion for PCT/US2019/021031 mailed on Jun. 18, 2019.
International Search Report and Written Opinion issued in PCT/US2018/034723 mailed Sep. 5, 2018.
International Search Report and Written Opinion received for PCT Patent Application No. PCT/US2020/030589, mailed on Jul. 17, 2020, 7 pages.
International Search Report and Written Opinion received for PCT Patent Application No. PCT/US21/042753, mailed on Nov. 5, 2021, 14 pages.
International Search Report and Written Opinion received for PCT Patent Application No. PCT/US21/14656, mailed on Apr. 28, 2021, 8 pages.
International Search Report and Written Opinion received for PCT Patent Application No. PCT/US21/14656, mailed or Apr. 28, 2021, 8 pages.
International Search Report and Written Opinion, PCT App. No. PCT/US2020/013754, mailed on Jun. 9, 2020, 11 pages.
Non-Final Office Action received for U.S. Appl. No. 15/606,607, mailed on Jun. 10, 2020, 26 pages.
European Search Report received for EP Patent Application No. 23188821.5, mailed on Dec. 6, 2023, 7 pages.
Office Action received for European Patent Application No. 19710207.2, mailed on Dec. 4, 2023, 4 pages.
Supplementary European Search Report received for EP Patent Application No. 21744674.9, mailed on Feb. 7, 2024, 9 pages.
Final Office Action received for U.S. Appl. No. 17/036,302, mailed on Jul. 30, 2024, 17 pages.
Final Office Action received for U.S. Appl. No. 17/382,271, mailed on Sep. 16, 2024, 9 pages.
Requirement for Restriction/Election received for U.S. Appl. No. 17/493,281, mailed on Oct. 9, 2024, 13 pages.
European Search Report received for EP Patent Application No. 21878402, mailed on Aug. 14, 2024, 13 pages.
Intention to grant received for European Patent Application No. 23188821.5, mailed on Aug. 14, 2024, 6 pages.
Non-Final Office Action received for U.S. Appl. No. 16/616,220, mailed on Nov. 5, 2024, 24 pages.
Non-Final Office Action received for U.S. Appl. No. 18/661,472, mailed on Dec. 6, 2024, 20 pages.
Requirement for Restriction/Election received for U.S. Appl. No. 18/589,282, mailed on Dec. 30, 2024, 5 pages.
Office Action received for U.S. Appl. No. 14/199,675, mailed on Nov. 3, 2016.
Office Action received for U.S. Appl. No. 15/611,328, mailed on Mar. 27, 2019.
U.S. Appl. No. 12/753,836, filed Feb. 1, 2012, Office Action.
U.S. Appl. No. 16/212,425, filed Dec. 6, 2018, by Christian.

* cited by examiner

MICRO-FABRICATED MEDICAL DEVICE HAVING A NON-HELICAL CUT ARRANGEMENT

CROSS-REFERENCE TO RELATED APPLICATIONS

This application is a divisional of U.S. application Ser. No. 16/616,139, filed Nov. 22, 2019, which is a 35 U.S.C. § 371 nationalization of PCT/US2018/034756, filed May 25, 2018, which claims priority to and the benefit of U.S. Provisional Patent Application Ser. No. 62/511,605, filed on May 26, 2017, and to U.S. Provisional Patent Application Ser. No. 62/595,425, filed on Dec. 6, 2017. Each of the foregoing applications is incorporated herein by this reference in its entirety.

BACKGROUND

Interventional devices such as guidewires and catheters are frequently utilized in the medical field to perform delicate procedures deep within the human body. Typically, a catheter is inserted into a patient's femoral, radial, carotid, or jugular vessel and navigated through the patient's vasculature to the heart, brain, or other targeted anatomy as required. Often, a guidewire is first routed to the targeted anatomy, and one or more catheters are subsequently passed over the guidewire and routed to the targeted anatomy. Once in place, the catheter can be used to deliver drugs, stents, embolic devices, radiopaque dyes, or other devices or substances for treating the patient in a desired manner.

In many applications, such an interventional device must be angled through the tortuous bends and curves of a vasculature passageway to arrive at the targeted anatomy. For example, directing a guidewire and/or catheter to portions of the neurovasculature requires passage through the internal carotid artery and other tortuous paths. Such an interventional device requires sufficient flexibility, particularly closer to its distal end, to navigate such tortuous pathways. However, other design aspects must also be considered. For example, the interventional device must also be able to provide sufficient torquability (i.e., the ability to transmit torque applied at the proximal end all the way to the distal end), pushability (i.e., the ability to transmit axial push to the distal end rather than bending and binding intermediate portions), and structural integrity for performing intended medical functions.

With respect to torquability, as a greater length of an interventional device (such as a guidewire) is passed into and through a vasculature passageway, the amount of frictional surface contact between the guidewire and the vasculature tissue increases, hindering easy movement through the vasculature passage. By transmitting torqueing forces from the proximal end to the distal end allows the guidewire to rotate and overcome the frictional forces so that further advancement and positioning is possible.

BRIEF SUMMARY

The present disclosure relates to interventional devices (such as guidewires and catheters) which have micro-fabricated features for providing flexibility while maintaining good torquability. In one embodiment, an interventional device includes an elongated member having a wall and an interior lumen. The elongated member includes a plurality of fenestrations which define a plurality of axially extending beams and a plurality of circumferentially extending rings. The beams are arranged along the length of the elongated member to form a non-helical and non-linear pattern functioning to optimally distribute bending axes to beneficially minimize or eliminate preferred bending directions of the elongated member.

Some interventional devices include cuts/fenestrations intended to increase flexibility at certain sections of the interventional device. However, typical guidewire and catheter devices including these features end up with one or more preferred bending directions as a result of the structural arrangement and spacing of the fenestrations. Although potentially useful in some applications, preferred bending directions often have a detrimental effect on the navigation capabilities of the device. For example, in some circumstances where an operator is attempting to reach a targeted anatomical area, the preferred bending direction(s) will tend to make the device "snap" toward a preferred bending direction. If the preferred bending direction is not aligned with the desired direction of movement, it can be difficult for the operator to guide the device to the target.

Some interventional devices include fenestrations formed in a helical arrangement along a length of the device. While such helical arrangements may be more beneficial than a simple alternating cut pattern in reducing preferred bending bias, the helical arrangement can itself form undesirable preferred bending patterns within the device. For example, an interventional device having a helical cut pattern is more likely to coil or twist into a curved shape that coincides with the direction of helical rotation about the device as opposed to curving in the opposite direction. In certain anatomical circumstances, this tendency may introduce navigation difficulties and/or may inhibit the user's ability to smoothly control the device.

One or more embodiments described herein are configured with a cut pattern which effectively distributes bending bias to minimize or eliminate preferred bending directions along the length of the device. The beneficial cut patterns are arranged in a non-helical and non-linear fashion to additionally avoid the shape bias inherent in devices relying on helical or linear cut patterns.

For convenience, the present disclosure may occasionally refer to "segments" of the elongated member. As used herein, a "segment" is a repeating structural unit of the elongated member. In a typical two-beam configuration, a single segment can be defined as a first pair of opposing beams disposed between two adjacent rings (one proximal ring and one distal ring) and a second pair of opposing beams extending from the distal ring and being rotationally offset by about 90 degrees from the first pair of opposing beams. In some embodiments, rotational offsets are applied at the segment to segment level rather than at every successive beam pair.

A distributed cut pattern provides rotational offsets that optimally spread preferred bending axes using a minimal length of the elongated member and/or using a minimal number of cuts. The distributed cut pattern beneficially maximizes the likelihood that the device includes a bending axis aligned with a bend required to navigate patient vasculature. Embodiments of distributed cut patterns as disclosed herein can achieve these effects by distributing individual bending axes in many different directions using a minimal number of cuts and within a short length of the device.

For example, for a given length of the elongated member, the radial spacing/distribution of possible beam positions is maximized in as short a length as possible (i.e., in as few number of cuts as possible) while keeping successive rotational offsets within a rotational offset limit. The rotational offset limit sets a limit for the allowable rotation of a beam pair given the positions of previous beam pairs. A rotational offset limit can minimize the effects of rigid spacing artifacts in the device. In some embodiments, the rotational offset limit from one segment to the next is about 10 to 30 degrees (i.e., 10 to 30 degrees from the beam pair two pairs prior).

In some embodiments, successive segments are positioned to form an imperfect ramp pattern. An imperfect ramp pattern is formed by intentionally disrupting an otherwise helix-like pattern with a series of purposefully designed imperfections. In an imperfect ramp pattern, beams are arranged such that no set of three successive segments or beam pairs are spaced according to the same rotational offset. In other words, if the cylindrical surface of the elongated member were unrolled into a plane, no set of three segments or beam pairs would form a straight line. The imperfect ramp pattern includes a variable rotational offset that can vary from one segment to the next by 5 to 15 degrees, for example.

In some embodiments, successive beam pairs or segments are positioned to form a sawtooth pattern. A sawtooth pattern includes a rotational offset that periodically reverses direction along the length of the elongated member. Whereas a typical helical pattern simply continues the rotational offset in the same direction through multiple rotations around the circumference of the elongated member, a sawtooth pattern reaches a first apex position before reversing direction and continuing toward a second apex position. Upon reaching the second apex position, the sawtooth pattern then reverses again and continues back toward the first apex. The pattern then repeats in this fashion along the desired length of the elongated member. In a two-beam configuration, the first and second apexes may be separated by about 90 degrees, for example.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION

Introduction

Figure 1:
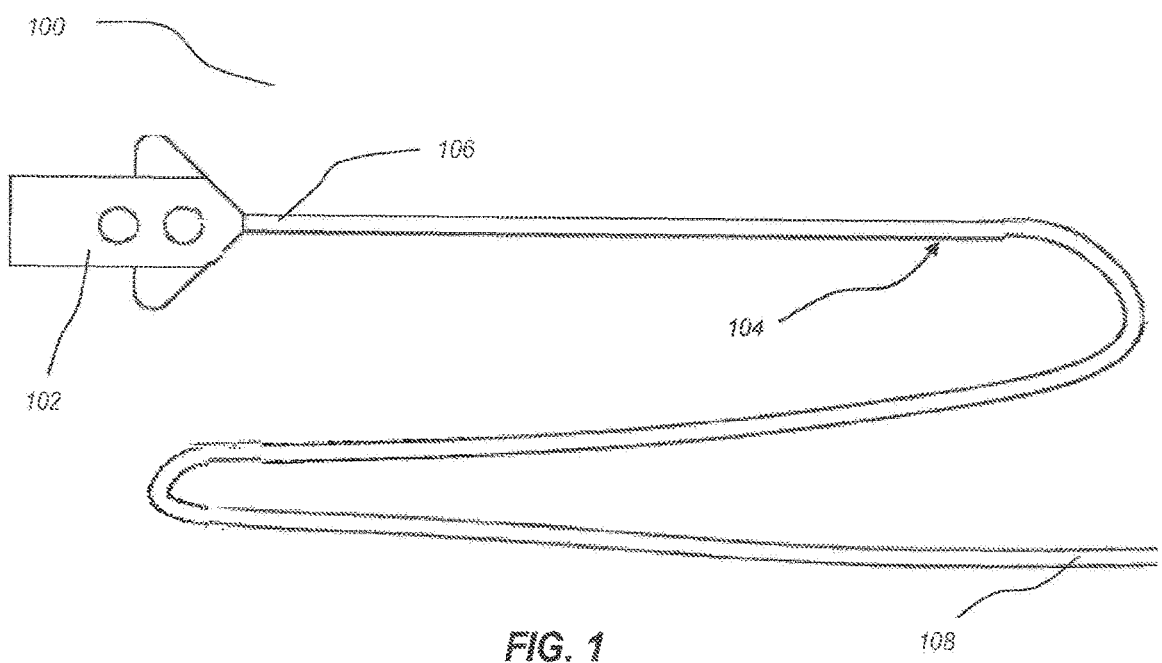
FIG. 1 illustrates an exemplary interventional device which may include beneficial micro-fabricated features described herein.

The present disclosure relates to interventional devices such as guidewires and catheters having micro-fabricated features which provide flexibility while also maintaining effective torquability and pushability for effective navigation through tortuous vasculature. The micro-fabricated features described herein include cut patterns which form fenestrations arranged to increase flexibility of the interventional device while maintaining good torquability and without forming preferred bending directions.

Cut patterns described herein may have different configurations defined by the number of beams resulting from each set of cuts at a given longitudinal position along the elongated member. For example, in a "two-beam" configuration, each cut location along the length of the device includes a pair of opposed cuts resulting in a pair of opposed, axially extending beams. Typically, the two beams within the resulting beam pair are symmetrically spaced about the circumference of the elongated member (i.e., spaced 180 degrees apart). Because of this 180 degree radial symmetry, a beam pair at a zero degree position will be indistinguishable from a beam pair rotationally offset by 180 degrees. Accordingly, throughout this disclosure, the possible rotational positions for beam pairs are described as ranging from 0 to 180 degrees, with the zero and 180 degree positions being equal to one another.

While the majority of the following description will be dedicated to embodiments having a two-beam configuration, it will be understood that the same principles may also be applied to "one-beam" configurations, "three-beam" configurations, and configurations having more than three beams at each cut location. It will also be understood that in such configurations the differing angular symmetries will require some adjustments to the values used in a two-beam configuration. For example, whereas each pair of cuts in a two-beam configuration will exhibit 180 degree radial symmetry, each cut in a one-beam configuration will not exhibit radial symmetry, each trio of cuts in a three-beam configuration will exhibit 120 degree radial symmetry, each set of four cuts in a four-beam configuration will exhibit 90 degree radial symmetry, etcetera. As such, the space of possible distinguishable rotational positions in a three-beam configuration will range from 0 to 120 degrees, in a four-beam configuration will range from 0 to 90 degrees, and so on. In a one-beam configuration, the space of possible rotational positions will range from 0 to 360 degrees.

Continuing with the example of a two-beam configuration, each pair of cuts at a given cut location dictates the rotational position of the resulting beams, and the rotational position of the resulting beams dictates the preferred bending axis at that location. For a given length of the elongated member, the relative rotational positioning of successive beam pairs determines the type and magnitude of preferred bending axes throughout the elongated member.

Typically, each successive beam pair is rotated 90 degrees plus a constant modifying value from the previous beam pair. In a "linear" cut pattern, the modifying value is zero, providing a constant rotational offset of 90 degrees from one beam pair to the next along the axial length of the elongated member, meaning successive beam pairs will alternate between a zero degree position and a 90 degree rotational position. This type of cut pattern leaves the elongated member with preferred bending axes at zero and 90 degrees for the length of the elongated member. If the modifying value is 5 degrees, for example, a "helical" cut pattern with helically distributed bending axes will result.

In contrast to such linear and helical cut patterns, the embodiments described herein provide effective distribution of individual bending axes to minimize preferred bending directions in the device. This beneficially provides the device with effective navigation capabilities for navigating patient vasculature.

Overview of Interventional Devices

FIG. 1 illustrates an interventional device 100 (e.g., a catheter or guidewire device) including a handle or hub 102 and an elongated member 104. The elongated member 104 has a proximal end 106 coupled to the hub 102 and a distal end 108 extending away from the hub 102. The hub 102 may include paddles, handles, grips, or the like allowing a user to grasp the device, rotate, push/pull, and otherwise manipulate the device 100. The elongated member 104 may be formed as a guidewire or as a catheter. Some embodiments such as guidewires may omit the hub 102 and may be used with accessories such as a torque device.

The elongated member 104 includes a plurality of fenestrations cut into its outer surface. The fenestrations may be formed by cutting one or more pieces of stock material to form a cut pattern which leaves the fenestrations. The fenestrations can provide a variety of benefits, including increasing the flexibility/bendability of the elongated member 104. In some embodiments, the fenestrations are arranged to provide enhanced flexibility (relative to a similar section of stock material lacking fenestrations) while maintaining sufficient outer circumferential structure for transmitting torque and thereby maintaining good torquability of the elongated member 104.

The elongated member 104 may be any length necessary for navigating a patient's anatomy to reach a targeted anatomical area. A typical length may be within a range of about 50 to 300 cm, for example. In a catheter embodiment, the outer diameter of the elongated member 104 may be within a range of about 0.010 inches to about 0.150 inches, though larger or smaller diameters may also be utilized according to preferences and/or application needs. In a guidewire embodiment, the outer diameter of the elongated member 104 may be about 0.014 inches, or may be within a range of about 0.008 to 0.145 inches, though larger or smaller sizes may also be utilized according to user preferences and/or application needs.

The elongated member 104, in a catheter embodiment, is typically formed from a material having an elastic modulus of about 3000 MPa to about 4500 MPa, or about 3500 MPa to about 4000 MPa. In one exemplary embodiment, the elongated member 104 is formed from or includes polyether ether ketone (PEEK). Other polymers with higher moduli may also be utilized where cost and/or fabrication considerations warrant it. In some embodiments, the elongated member 104 includes or is formed from a nickel-titanium alloy having superelastic properties at body temperature. In some embodiments, a proximal portion of the elongated member 104 is formed from a stainless steel or other material with similar stress-strain and elastic modulus properties. Typically, if the elongated member 104 is formed from two or more different materials, the higher modulus material(s) are used at more proximal sections and the lower modulus material(s) are used at more distal sections.

Figure 2:
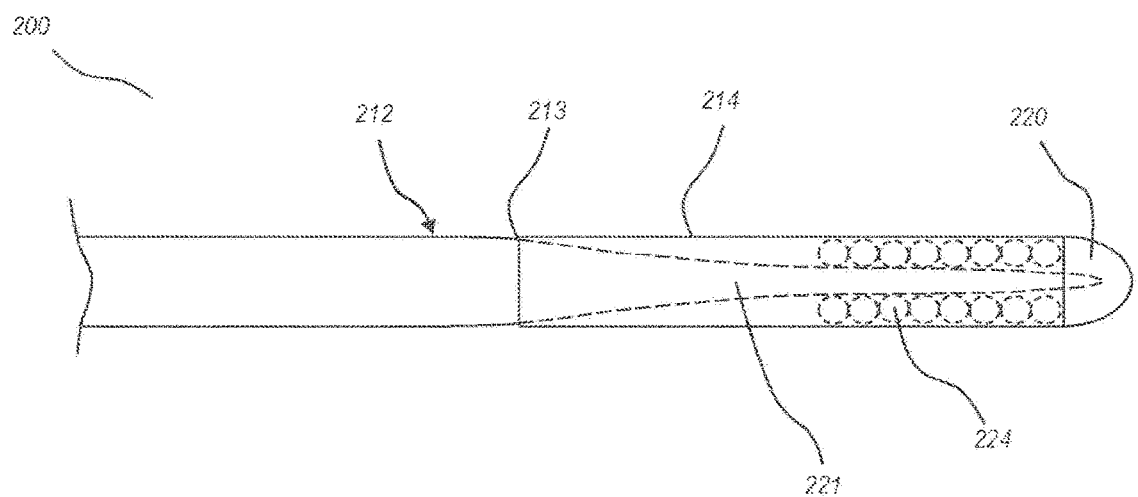
FIG. 2 illustrates a distal section of an exemplary guidewire device which may include beneficial micro-fabricated features described herein.

FIG. 2 illustrates the distal end of an embodiment of an interventional device configured as a guidewire 200. The embodiment illustrated in FIG. 2 may represent the distal end 108 of a guidewire embodiment of the elongated member 104 of FIG. 1. The illustrated guidewire 200 includes a core 212 and a tube structure 214 coupled to the core 212. As shown, a distal section 221 of the core 212 extends into the tube 214 and is surrounded by the tube 214. In some embodiments, the distal section 221 of the core 212 is ground so as to progressively taper to a smaller diameter (e.g., about 0.002 inches) at the distal end. The distal section 221 of the core 212 may have a round cross-section, rectangular cross-section, or other suitable cross-sectional shape. In this example, the core 212 and the tube 214 have substantially similar outer diameters at the attachment point 213 where they adjoin and attach to one another.

The tube 214 is coupled to the core 212 (e.g., using adhesive, soldering, and/or welding) in a manner that allows torsional forces to be transmitted from the core 212 to the tube 214 and thereby to be further transmitted distally by the tube 214. A medical grade adhesive 220 may be used to couple the tube 214 to the core 212 at the distal end of the device and to form an atraumatic covering.

The guidewire 200 may also include a coil 224 disposed within the tube 214 so as to be positioned between an outer surface of the distal section of the core 212 and an inner surface of the tube 214. The coil 224 may be formed from a radiopaque material, such as platinum. The illustrated coil 224 is formed as one integral piece. In alternative embodiments, the coil 224 includes a plurality of separate sections stacked, positioned adjacent to one another, and/or interlocked through intertwining.

The tube 214 includes micro-fabricated fenestrations configured to provide effective flexibility and torquability of the interventional device without forming preferred bending directions. Some embodiments may additionally or alternatively include cuts formed in the core 212 itself, such as along the distal section 221 of the core.

Cut Patterns

Figure 3A:
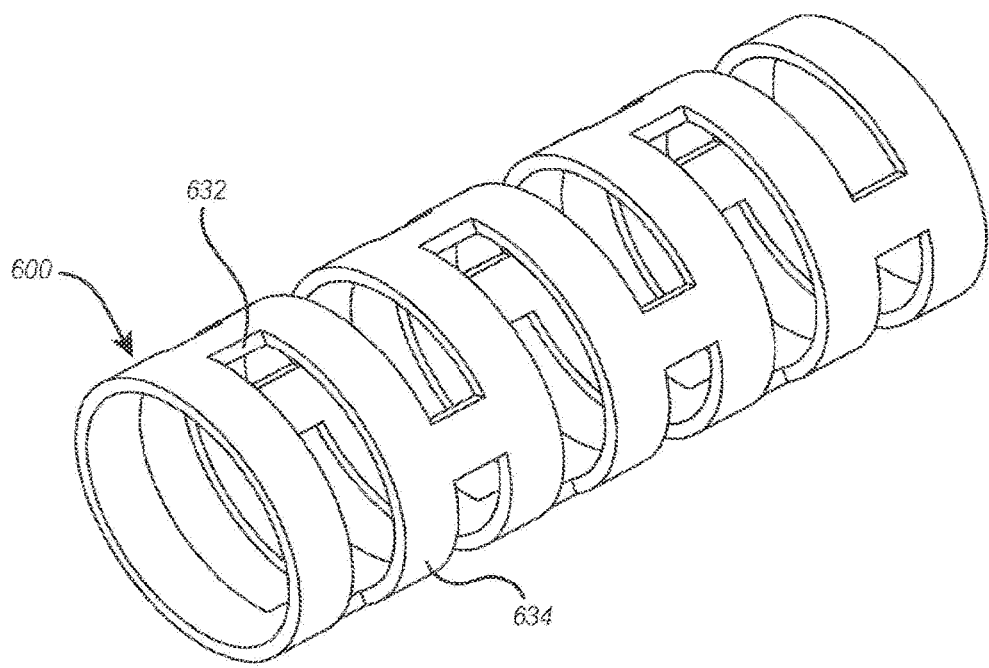
FIGS. 3A through 3C illustrate various elongated members having linear cut patterns.
Figure 3B:
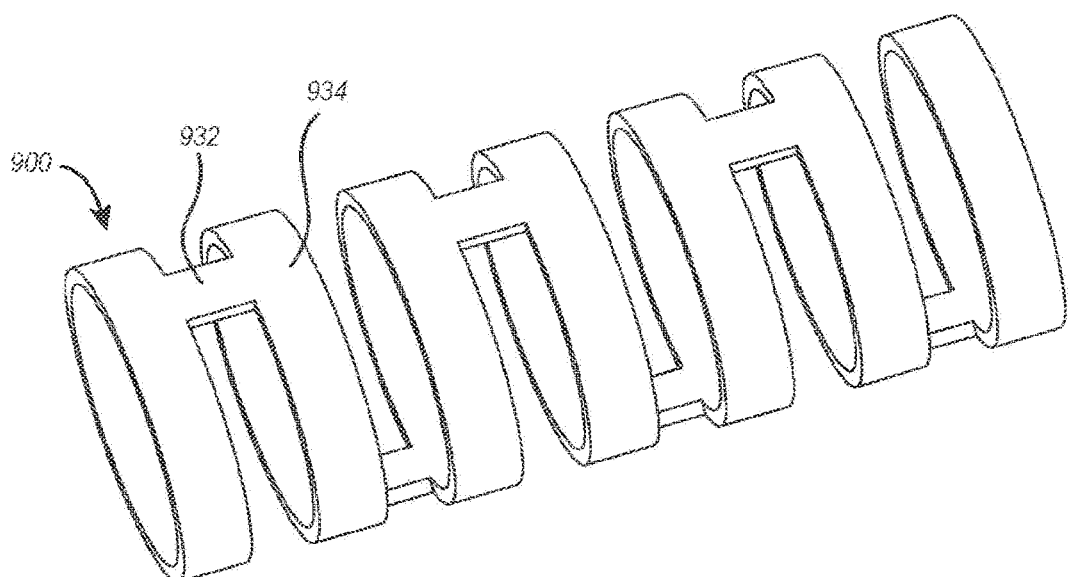
Figure 3C:
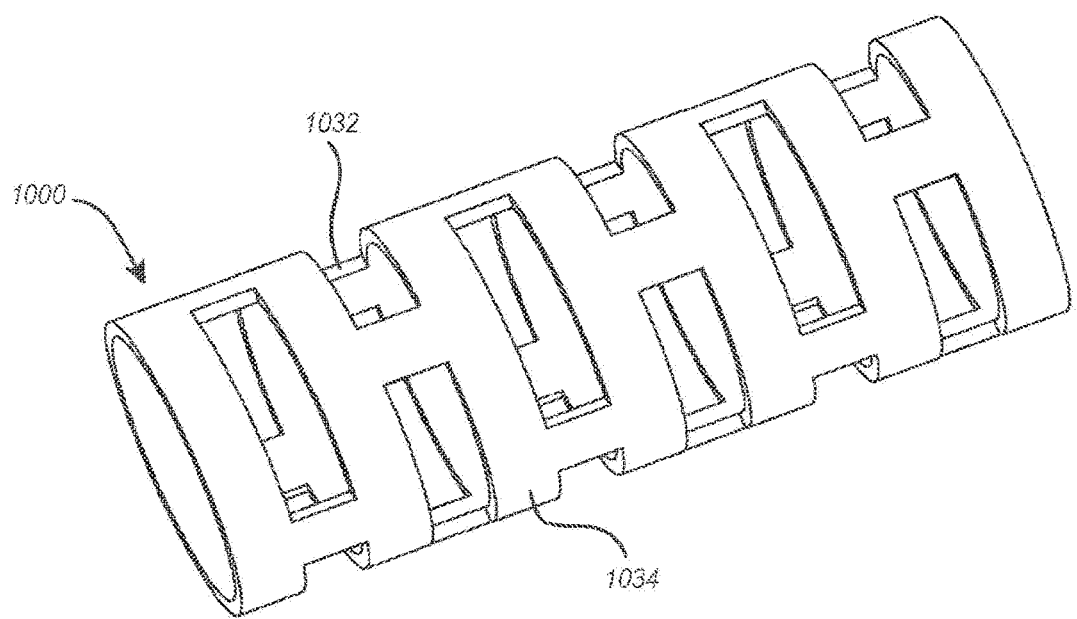

FIGS. 3A through 3C illustrate embodiments of linear cut patterns, with FIG. 3A showing a typical "two-beam" linear cut pattern, FIG. 3B showing a typical "one-beam" linear cut pattern, and FIG. 3C showing a typical "three-beam" linear cut pattern.

As shown in FIG. 3A, the elongated member 600 includes a plurality of axially extending beams 632 and circumferentially extending rings 634. The elongated member 600 has a two-beam cut pattern because two circumferentially opposing beams 632 are disposed between each pair of adjacent rings 634. The illustrated cut pattern is a linear cut pattern because no rotational offset is applied from one segment to the next.

As described above, a "segment" is a repeating structural unit of the elongated member. In some embodiments, a single segment can be defined as a first pair of opposing beams 632 disposed between two adjacent rings 634 (one proximal ring and one distal ring) and a second pair of opposing beams 632 extending from the distal ring and being rotationally offset by about 90 degrees from the first pair of opposing beams 632. The linear arrangement of segments results in the formation of preferred bending directions aligned to the fenestrations of the elongated member 600.

FIG. 3B illustrates an elongated member 900 having a plurality of beams 932 and rings 934. The elongated member 900 is an example of a one-beam cut pattern because a single beam 932 is disposed between each pair of adjacent rings 934. In such a one-beam cut pattern, a single segment may be defined as a first beam 934 disposed between two adjacent rings 934 (one proximal ring and one distal ring) and a second beam 932 extending from the distal ring and being rotationally offset by about 180 degrees from the first beam 932. As with the elongated member 600, the elongated member 900 has a linear cut pattern because no rotational offset is applied from one segment to the next.

FIG. 3C illustrates an elongated member 1000 having a plurality of beams 1032 and rings 1034. The elongated member 1000 is an example of a three-beam cut pattern because three beams 1032 are disposed between each pair of adjacent rings 1034. In such a three-beam cut pattern, a single segment may be defined as a first triplicate of beams 1032 disposed between two adjacent rings 1034 (one proximal ring and one distal ring) and a second triplicate of beams 1032 extending from the distal ring and being rotationally offset by about 60 degrees from the first triplicate. As with the elongated members 600 and 900, the elongated member 1000 has a linear cut pattern because no rotational offset is applied from one segment to the next.

From the foregoing examples it will be understood that a variety of cut patterns may be utilized. For example, cut patterns providing more than three beams between each pair of adjacent rings may be utilized according to particular application needs. Generally, the higher the number of beams left between each pair of adjacent rings, the relatively greater the stiffness of the elongated member.

Figure 4:
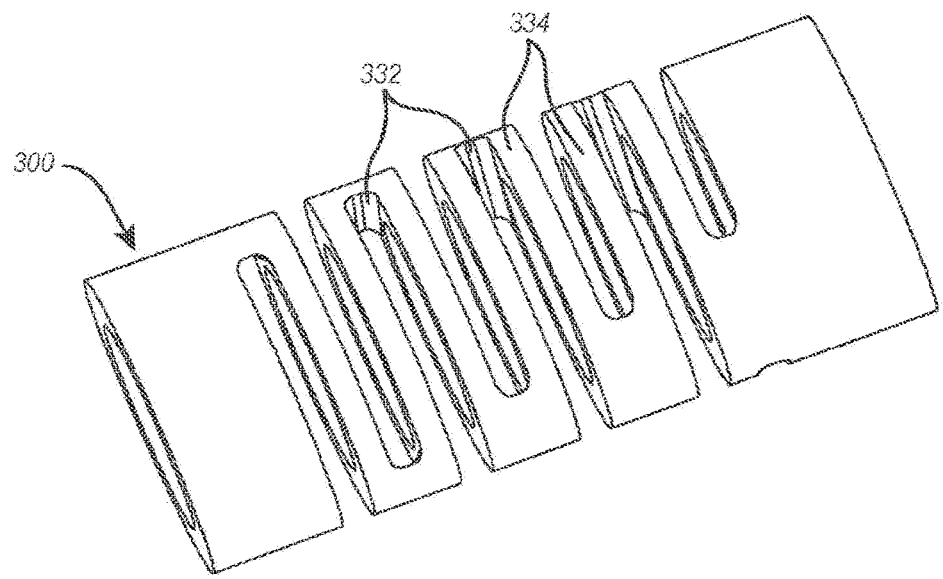
FIG. 4 illustrates an elongated member having a conventional helical cut pattern.

FIG. 4 illustrates an embodiment of a typical helical cut pattern intended to minimize preferred bending directions in a micro-fabricated guidewire or catheter device. As shown, cuts made to the elongated member 300 leave pairs of opposing beams situated on opposing sides of the longitudinal axis of the hollow member. Each pair of such cuts forms two beams 332 (extending substantially axially) connecting adjacent rings 334 (extending substantially transversely and circumferentially).

A rotational offset is applied at each successive segment of the elongate member 300 to form the helical pattern. As used herein, a "rotational offset" is the angular rotation between two adjacent segments. A rotational offset is therefore applied from one segment to the next, even though individual cuts within a segment may also be offset from one another.

In a typical embodiment, a single segment can be defined as a first pair of opposing beams 332 disposed between two adjacent rings 334 (one proximal and one distal) and a second pair of opposing beams 332 extending from the distal ring and being rotationally offset by about 90 degrees from the first pair of opposing beams 332. The cuts are arranged to form a substantially consistent rotational offset from one segment to the next. For example, the illustrated embodiment shows a rotational offset of about 5 degrees from one segment to the next. When multiple successive segments having such an angular offset are formed, the resulting pattern of beams along a sufficient length of the elongated member 300 wraps around the axis of the elongated member 300 in a continuously rotating helical pattern.

This type of helical arrangement may also be used in embodiments having different cut patterns. For example, an elongate member having a "one-beam" or "bypass" cut pattern where each cut leaves a single beam between each set of adjacent rings may have a constant rotational offset between each successive cut or set of cuts.

A helical arrangement may also be applied to an embodiment having more than a two-beam cut pattern. For example, the same helix-forming rotational offset may be applied to a three-beam embodiment (such as shown in FIG. 3C) or to an embodiment having more than three beams between adjacent rings.

Helical cut patterns such as that shown in FIG. 4 can beneficially minimize some of the preferred directional bending tendencies of an elongate member. However, the helical structure itself defines a preferred bending curve. An elongated member having a helical cut pattern is more likely to coil or twist into a curve that coincides with the direction of helical rotation as opposed to curving in the opposite direction.

Distributed Patterns

Figure 5:
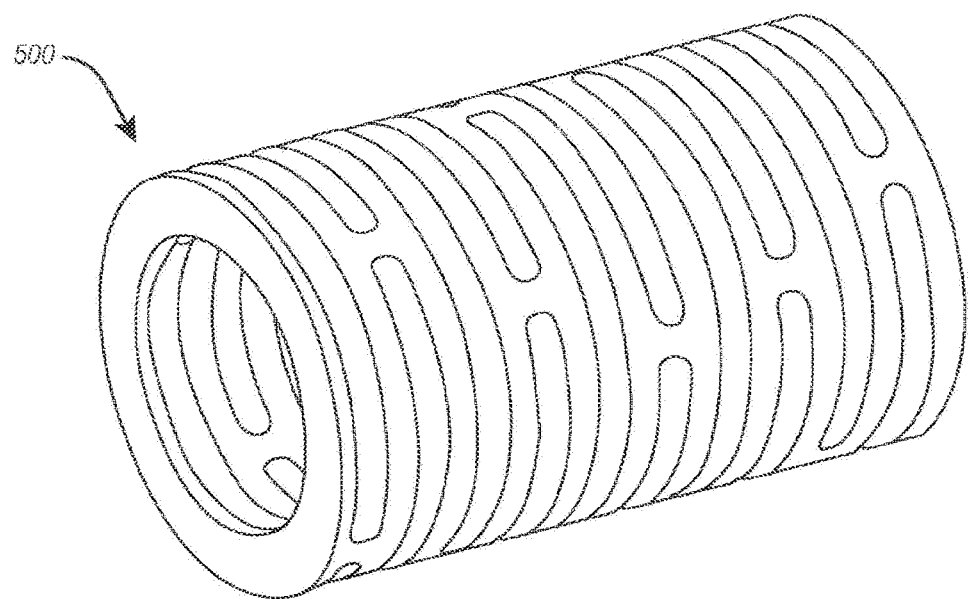
FIG. 5 illustrates an example of an elongated member having a non-helical and non-linear cut pattern (distributed cut pattern) for beneficially distributing bending axes and minimizing or reducing preferred bending directions.

FIG. 5 illustrates a section of an elongated member 500 with a distributed cut pattern. The cuts are beneficially arranged to efficiently distribute the rotational spacing of each beam pair. In this manner, the non-helical and non-linear cut pattern effectively eliminates or minimizes preferred bending directions along the length of the elongated member 500. The cut pattern shown in FIG. 5 is "non-helical" because, in contrast to a helical cut pattern, the resulting beams of the elongated member 500 are not arranged in a helical pattern around axis of the elongated member 500.

The cut pattern shown in FIG. 5 is also "non-linear" because there is a rotational offset applied at successive segments of the device, and because the rotational offsets applied to the segments making up the elongated member 500 are not necessarily equal or constant from one segment to the next.

A helix is commonly defined as following a curve on a conical or cylindrical surface that would become a straight line if the surface were unrolled into a plane. Using the helical cut pattern shown in FIG. 4 as an example, any curved lines tracing the arrangement of the beams/segments along the length of the elongated member 300 would form straight lines if the elongated member 300 were cut open and "unrolled" into a plane. In contrast, using the cut pattern illustrated in FIG. 5, any lines tracing the arrangement of the beams/segments along the length of the elongated member 500 would not form straight lines. For example, given a set of any three successive beam pairs or segments along the length of the elongated member 500 of FIG. 5, the rotational positions of the three successive beam pairs or segments would not form a straight line if the elongated member 500 were unrolled into a plane.

A helix is also typically understood to require at least one full circumferential rotation about the conical/cylindrical surface it lies upon. As such, a cut pattern may also be considered non-helical where the resulting rotational arrangement of beam pairs or segments does not form a pattern that fully wraps around the circumference of the elongated member at least once before changing direction. For example, if the cylindrical surface of the elongated member were unrolled into a plane, and that plane included a series of three or more segments positionally aligned in a straight line, the series of segments would still not constitute a helix if the straight line does not wrap around the circumference of the elongated member at least once.

Rotational offsets may be applied from one beam pair to the next. Alternatively, rotational offsets may be applied to the elongated member at the segment to segment level. As described above, each segment of the elongated member may be defined as a first pair of opposing beams between a proximal and distal ring, and a second pair of beams extending from the distal ring which are offset by approximately 90 degrees from the first pair of beams. Alternative embodiments may apply the distributed rotational offset pattern between segments of different sizes and/or between segments with different internal offsets. For example, some embodiments may include segments having more than two pairs of beams (and more than two corresponding rings) and/or with internal offsets different than 90 degrees. Further, even though the illustrated example shows a two-beam cut pattern where each pair of the opposing cuts results in two circumferentially opposing beams, it will be understood that the distributed offset patterns may also be applied to one-beam cut patterns (see FIG. 3B), three-beam cut patterns (see FIG. 3C), and patterns having more than three beams between adjacent rings.

Figure 6A:
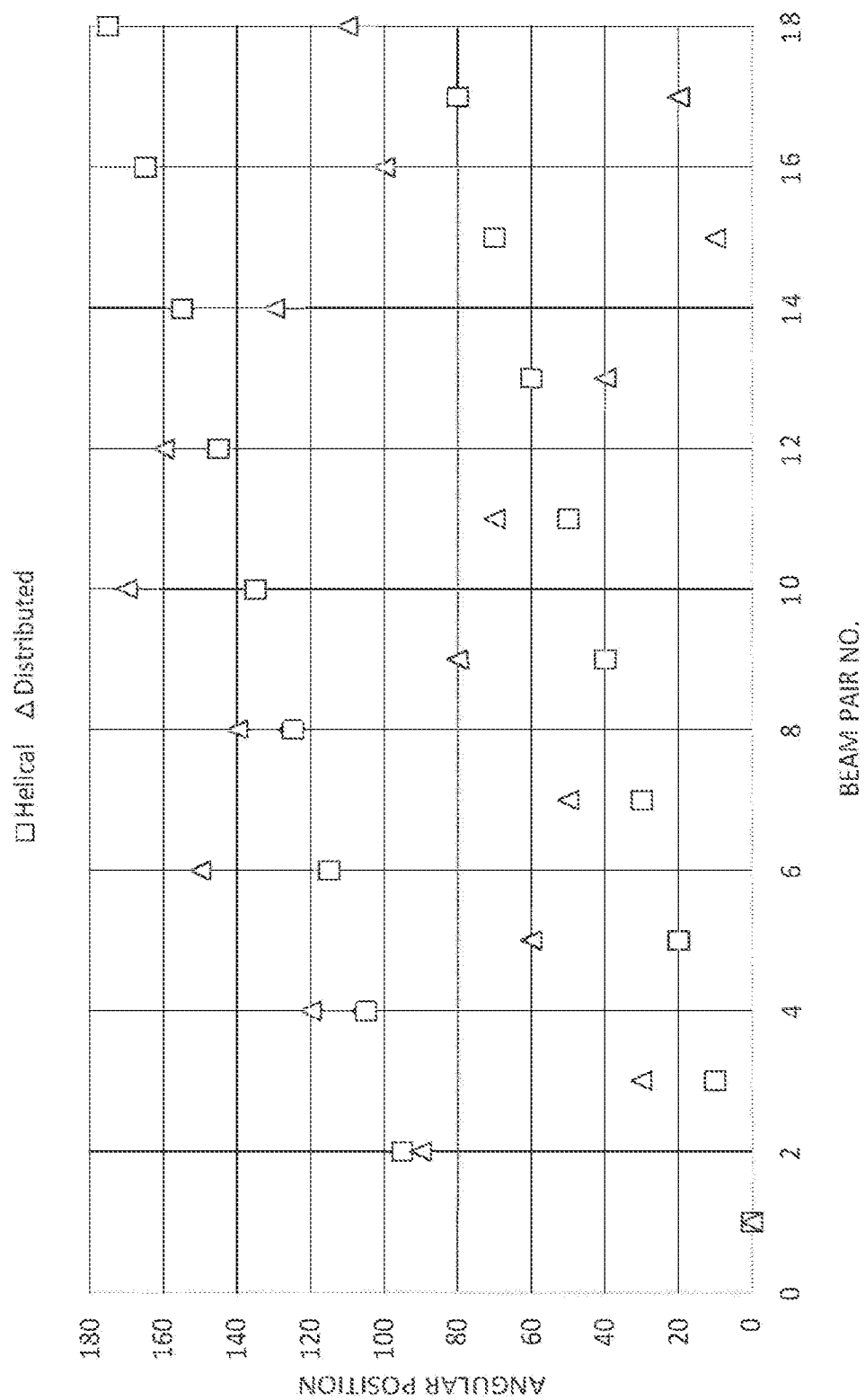
FIG. 6A illustrates exemplary beam pair positioning for forming a distributed, non-helical and non-linear cut pattern.

FIG. 6A graphically compares one example of a distributed arrangement with a conventional helical arrangement. As shown, the helical cut pattern applies a constant rotational offset from segment to segment along the length of the elongated member. The distributed cut pattern applies a rotational offset that effectively distributes bending axes without relying on a helical pattern.

Given a starting beam pair arbitrarily assigned to a zero degree position, successive beam pairs are rotationally offset to maximize the radial distribution of beam positions across the available 180 degree radial space as quickly as possible (i.e., in as few cuts as possible). However, in the illustrated embodiment, a rotational offset limit is also applied to prevent the formation of rigid spacing artifacts (discussed further below with respect to FIGS. 7 and 8).

The rotational offset limit defines a limit on the acceptable rotational "jump" from one beam pair to the next or from one segment to the next. A rotational offset limit with a value of about 10 to 30 degrees from one segment to the next, or a rotational offset limit that rotates successive beam pairs by 90 degrees±that value, has been shown to provide effective distribution of bending axes without causing overly rigid spacing artifacts. For example, the rotational offset limit may restrict rotation from one beam pair to the next to a value within a range of about 60 to 120 degrees, or about 70 to 110 degrees, or about 80 to 100 degrees. Other embodiments may utilize other rotational offset limits, or may even omit the rotational offset limit, depending on particular product and/or application needs. For example, the rotational offset limit may be raised to a value higher than 30 degrees if the resulting spacing artifacts are acceptable for a particular application.

The exemplary distributed cut pattern illustrated in FIG. 6A utilizes a rotational offset limit of 30 degrees. As shown, a first beam pair is positioned at an arbitrary 0 degree position, and the second beam pair is positioned at 90 degrees. The greatest remaining gaps in the available 180 degree space are between 0 and 90 degrees and between 90 and 180 degrees (where 0 and 180 degrees represent the same position). Placing the next beam pair near a midpoint of one of these gaps, such as at 45 degrees, would best distribute the bending axes of the device. However, placing the next beam pair at 45 degrees would violate the rotational offset limit of 30 degrees. The next beam pair is therefore placed to be close to the midpoint of a remaining gap without violating the rotational offset limit. In this example, the third beam pair is placed at 30 degrees. The fourth beam pair is placed at 120 degrees, which is 90 degrees from the third beam pair. In this particular example, every other beam pair is offset 90 degrees from the previous. Alternative embodiments need not necessarily follow this particular pattern.

Continuing with the example distribution of FIG. 6A, the largest remaining positional gaps are now between 30 and 90 degrees and between 120 and 180 degrees. The fifth and sixth beam pairs are placed at 60 and 120 degrees, respectively. The remaining positional gaps are now located every 30 degrees (i.e., between 0 and 30 degrees, between 30 and 60 degrees, between 60 and 90 degrees, etc.). As the pattern continues, remaining angular positions are filled in a manner that radially spaces beam pairs as fast as possible without violating the rotational offset limit.

In the illustrated example, the available angular positions are provided at a granularity of 10 degrees. In other words, all angular positions may be considered as filled when each 10 degree increment has been filled. The illustrated pattern may therefore includes beam pairs positioned at approximately every 10 degree position before resetting. Such an arrangement is referred to herein as having a "positional granularity" of 10 degrees. Alternative embodiments may utilize a different positional granularity, such as a granularity of 0.1, 0.5, 1, 3, 5, 10, 15, 18, 20, 25, or 30 degrees, for example.

The exact positioning illustrated may be adjusted, and it will be understood that the pattern shown in FIG. 6A is illustrative only. For example, the positional gaps may be filled using a different particular sequence as long as rotational jumps are within the predetermined rotational offset limit. Preferably, when filling in gaps between rotational positions, the next beam pair is positioned to be close to the approximate center of the largest remaining positional gap without violating the rotational offset limit. For example, where a gap exists between the zero degree position and the 30 degree position, the segment may be positioned at the 10 to 20 degree position.

Further, alternative embodiments may utilize a positional granularity that fills in positions of more or less than 10 degrees. Where fewer segments are used before resetting the pattern, the size range of each suitable position will be larger, and where more segments are used before resetting the pattern, the size ranges will become smaller. Some embodiments may include about 6 to 36 beam pairs, or about 10 to 18 beam pairs, before the availability of filled angular positions within the 180 degree radial space is reset. Other embodiments may include many more beam pairs before available positions are reset. As the predetermined positional granularity is lowered, the number of beam pairs needed to fill all available angular positions will rise. Thus, a device having a positional granularity of 1 degree will use 180 beam pairs to fill 180 available angular positions. Moreover, because there are multiple ways of filling available angular positions according to the predetermined parameters (e.g., positional granularity and rotational offset limit) of the selected distributed pattern, the distributed cut pattern need not identically repeat itself after resetting. Therefore, as used herein, the terms "reset," "resetting," and the like refer to resetting the availability of angular positions within the 180 degree radial space after it has been filled by beam pairs, and the terms do not necessarily imply that the subsequent refilling of angular positions along the next section of the elongated member will exactly repeat the previous pattern. Indeed, in at least some embodiments, the entire length of the distributed pattern may be non-repeating.

It will be understood that the foregoing principles may also be applied to an embodiment having a one-beam arrangement, an embodiment having a three-beam arrangement, or an embodiment having more than a three-beam arrangement. For example, the one-beam embodiment shown in FIG. 5 may be modified to follow a non-helical and non-linear cut pattern rather than the helical cut pattern shown. The same principles described above may be applied to a one-beam embodiment, except that the range of angular positions to fill extends to 360 degrees. Likewise, the same principles may be generally applied to a three-beam embodiment, except that the range of angular positions to fill extends to 120 degrees.

Imperfect Ramp Patterns

Figure 6B:
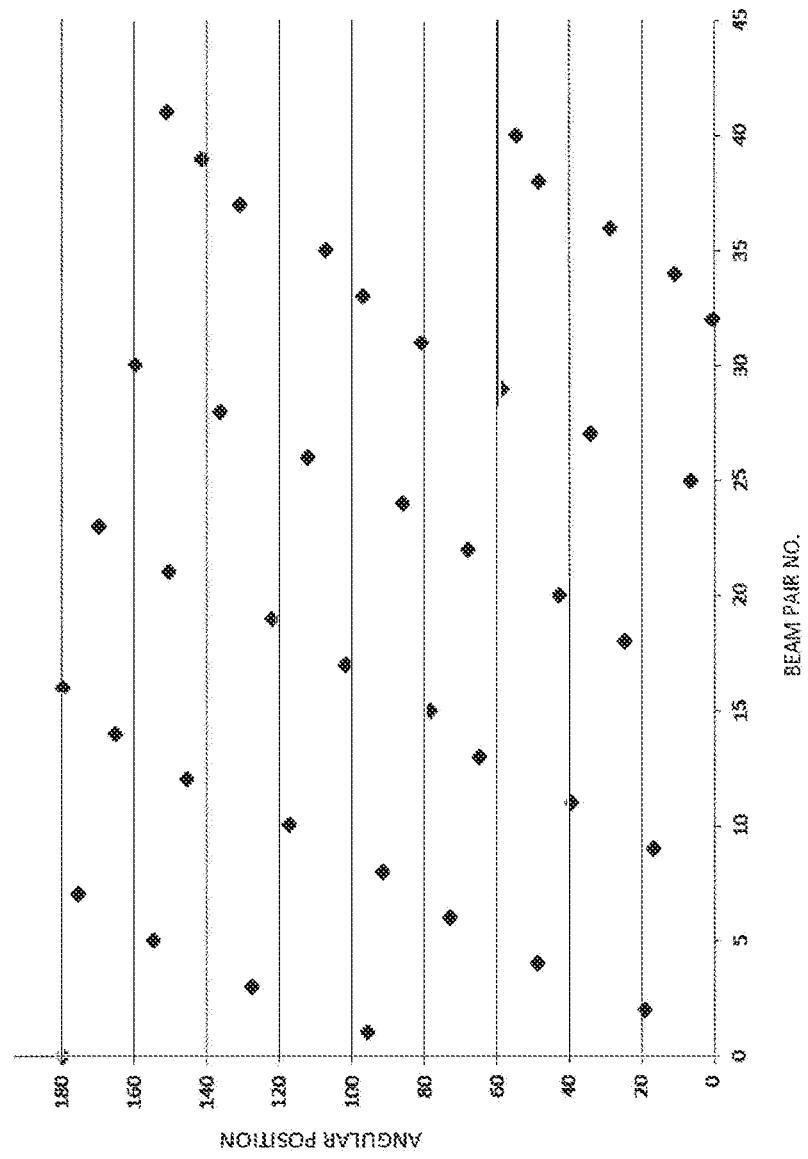
FIG. 6B illustrates exemplary beam pair positioning for forming an imperfect ramp cut pattern.

FIG. 6B graphically illustrates another embodiment of a non-helical cut pattern formed by intentionally disrupting an otherwise helical pattern with a series of purposefully designed imperfections. This type of cut pattern is referred to herein as an "imperfect ramp" pattern. The intentional divergences of an imperfect ramp pattern beneficially function to reduce or prevent preferred torsional and curvature relics inherent in a true helical arrangement. As shown, segments are arranged such that no three successive beam pairs or segments are spaced according to the same rotational offset. In other words, no three beam pairs or segments are arranged so as to form a straight line if the cylindrical elongated member were unrolled into a plane.

In contrast to the imperfect ramp patterns of FIG. 6B, a true helical pattern is typically formed by rotationally offsetting each successive segment or each successive beam pair by a constant value. For example, a true helical pattern in a two-beam structure may be formed by rotationally offsetting each successive cut pair by a constant value of 5 degrees, 85 degrees, 95 degrees, or some other constant value that is not a multiple of 90 degrees.

In an imperfect ramp cut pattern, the modifying value is intentionally made variable rather than constant. For example, as in FIG. 6B, an imperfect ramp pattern may be formed by rotationally offsetting each successive beam pair by a constant value±a variable modifying value. A rotational offset that includes a constant value±a variable modifying value is referred to herein as an "imperfect rotational offset."

The variable modifying value may range from 5 to 15 degrees. In other embodiments, the variable modifying value may range from 2.5 to 30 degrees, or some other range suitable for the intended purpose of the resulting device. The variable modifying value is preferably randomly selected at each segment or beam pair to which it is applied, with upper and lower bounds of the random selection being defined by the modifying value range (e.g., 5 to 15 degrees). The constant value portion of the offset is typically 180 degrees in a one beam pattern, 90 degrees in a two-beam pattern, 60 degrees in a three-beam pattern, etcetera.

Alternative embodiments may apply the imperfect ramp pattern between segments of different sizes and/or between segments with different internal offsets. For example, some embodiments may include segments having more than two pairs of beams (and more than two corresponding rings) and/or with internal offsets different than 90 degrees. Further, even though the illustrated example shows a two-beam cut pattern where each pair of the opposing cuts results in two circumferentially opposing beams, it will be understood that the distributed offset patterns may also be applied to one-beam cut patterns (see FIG. 3B), three-beam cut patterns (see FIG. 3C), and patterns having more than three beams between adjacent rings.

Sawtooth Patterns

Figure 6C:
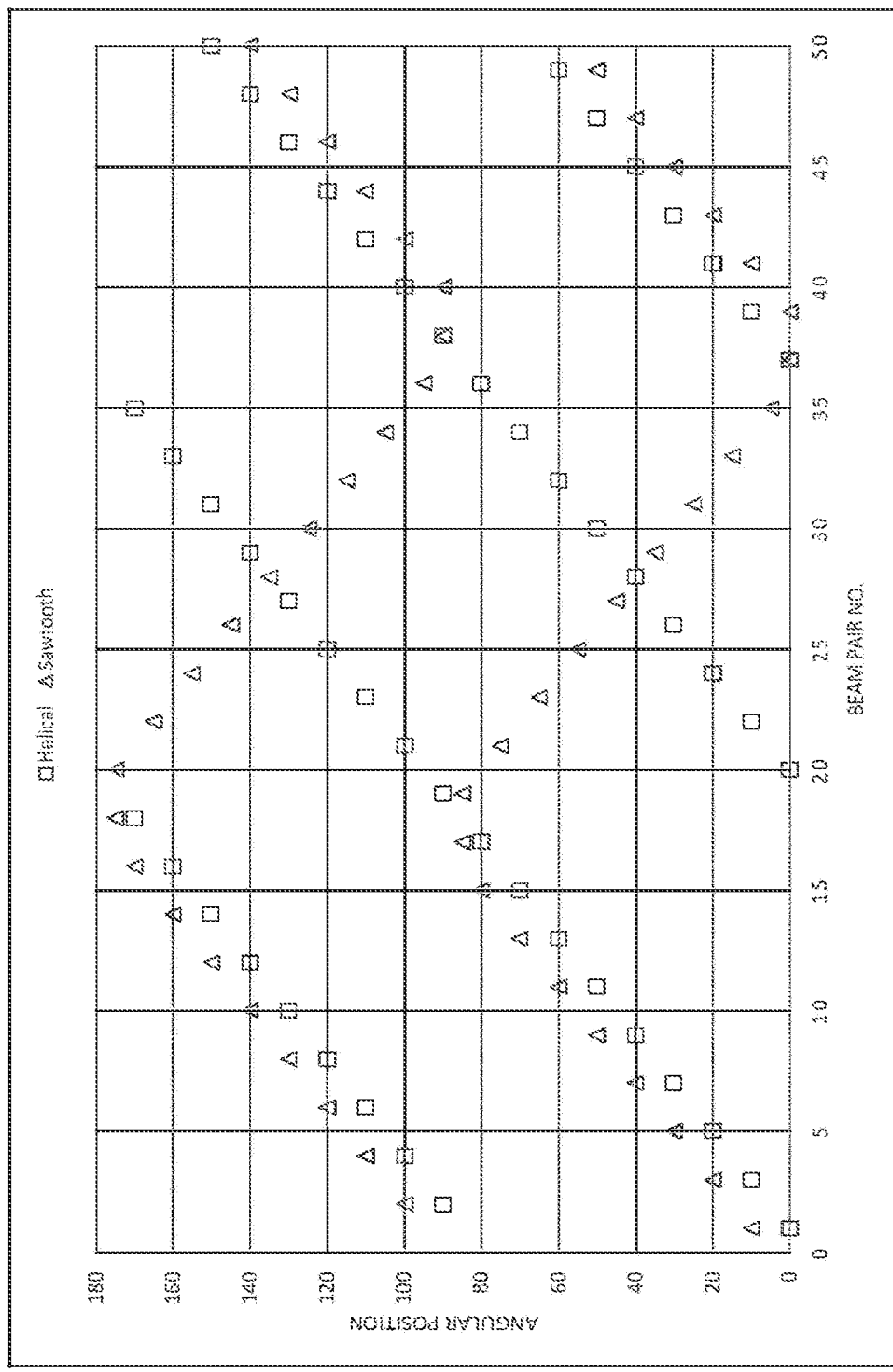
FIGS. 6C and 6D illustrate exemplary beam pair positioning for forming a sawtooth cut pattern.

FIG. 6C illustrates another embodiment of a non-helical cut pattern referred to herein as a "sawtooth" pattern. As with other non-helical cut patterns described herein, the sawtooth cut pattern can beneficially avoid preferred bending axes while also limiting preferred curvature directions inherent in helical patterns. In contrast to a helical pattern, a sawtooth cut pattern periodically reverses the direction of the rotational offset.

Both the sawtooth pattern and the helical pattern of FIG. 6C have an angular offset of about 10 degrees between adjacent segments, with each cut pair within each segment offset by 90 degrees. Whereas the helical pattern simply continues with these offset values in the same direction through multiple rotations around the circumference of the elongated member, the sawtooth pattern reaches a first apex position before reversing direction and continuing toward a second apex position. Upon reaching the second apex position, the sawtooth pattern then reverses again and continues back toward the first apex. The pattern then repeats along the desired length of the elongated member.

For example, the first apex position is set at about 90 degrees (i.e., 90 degrees for the first cut pair of the segment and 180 degrees for the second cut pair of the segment). Upon reaching the first apex position, the pattern reverses toward the second apex position. In this embodiment, the second apex position is set at about 0 degrees (i.e., 0 degrees for the first cut pair of the segment and 90 degrees for the second cut pair of the segment). Alternative embodiments may include other apex positions. Given an arbitrary zero degree starting position, the first apex position is less than 360 degrees in a one-beam configuration, less than 180 degrees in a two-beam configuration, less than 120 degrees in a three-beam configuration, and so on. Preferably, the first apex position is about 180 degrees for a one-beam configuration, 90 degrees for a two-beam configuration, 60 degrees for a three-beam configuration, and so on.

Figure 6D:
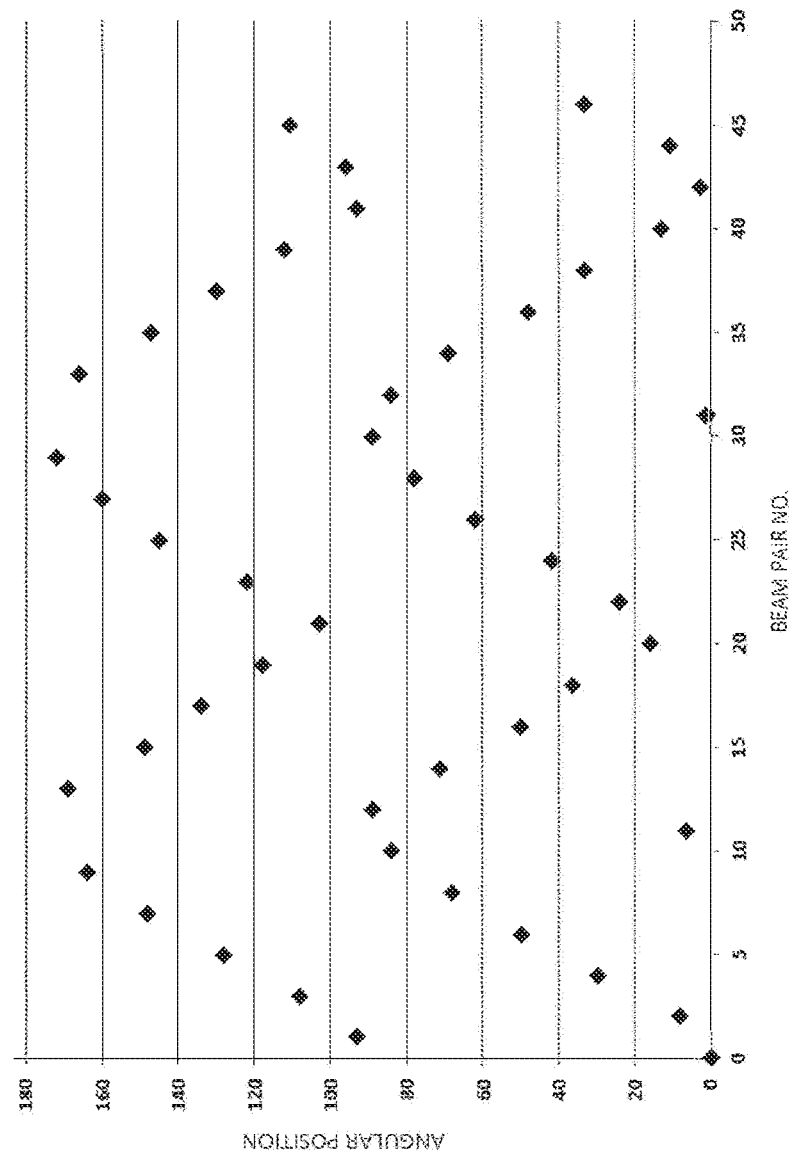

As described above, the angular offset from segment to segment in the sawtooth pattern of FIG. 6C is about 10 degrees. In other embodiments of sawtooth cut patterns, the angular offset may be more or less than 10 degrees, such as from about 5 degrees to about 30 degrees. Additionally, or alternatively, portions of the cut pattern between the apexes may include a variable offset. For example, one or more portions between the apexes may include an imperfect rotational offset such as described above. FIG. 6D illustrates one such embodiment. The sawtooth cut pattern shown in FIG. 6D follows a sawtooth pattern similar to the pattern shown in FIG. 6C, but also includes some sections of variable/imperfect rotational offset between the apexes.

Alternative embodiments may apply the sawtooth pattern between segments of different sizes and/or between segments with different internal offsets. For example, some embodiments may include segments having more than two pairs of beams (and more than two corresponding rings) and/or with internal offsets different than 90 degrees. Further, even though the illustrated example shows a two-beam cut pattern where each pair of the opposing cuts results in two circumferentially opposing beams, it will be understood that the distributed offset patterns may also be applied to one-beam cut patterns (see FIG. 3B), three-beam cut patterns (see FIG. 3C), and patterns having more than three beams between adjacent rings.

Spacing Artifacts

Figure 7:
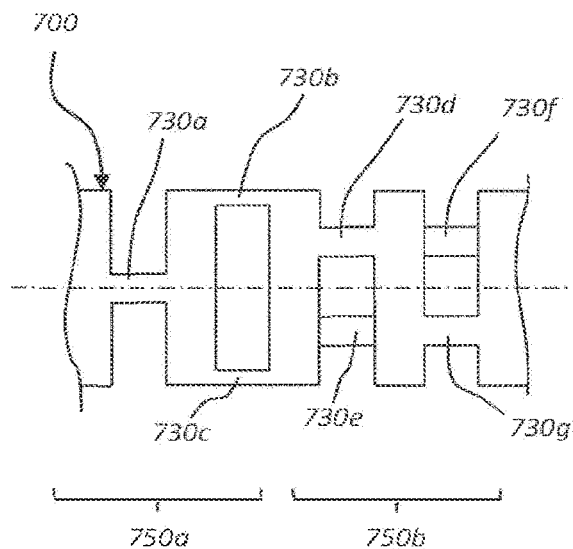
FIGS. 7 and 8 illustrate differences in rotational offsets, showing differences in spacing artifacts resulting from different sizes of rotational offset jumps.

FIG. 7 illustrates an example of an undesirable spacing artifact that may result where a rotational offset limit is not applied. FIG. 7 illustrates a section of an elongated member 700 having a first segment 750a and a second segment 750b. The first segment 750a includes a first pair of beams 730a (only one of which is visible in this view) and second pair of beams 730b and 730c which are offset from the first pair by 90 degrees. The second segment 750b includes a first pair of beams 730d and 730e, and a second pair of beams 730f and 730g which are offset from the first pair by 90 degrees. Each beam within a pair is circumferentially spaced from its corresponding beam by 180 degrees. The second segment 750b is offset from the first segment 750a by 45 degrees, which positions the first pair of beams 730d and 730e off by 45 degrees from the first pair of beams 730a and positions the second pair of beams 730f and 730g off by 45 degrees from the second pair of beams 730b and 730c.

Applying such a 45 degree offset from the first segment 750a to the second segment 750b is desirable because it places the bending axes of the second segment 750b in between the bending axes of the first segment 750a. However, the 45 degree jump also results in beam spacing between segments which can leave an overly rigid artifact in a portion of the elongated member 700. In the illustrated member 700, the beam 730d is only spaced from the beam 730b by 45 degrees, whereas the beam 730e is spaced from the beam 730b by 135 degrees. Likewise, the beam 730e is only spaced from the beam 730c by 45 degrees, whereas the beam 730d is spaced from the beam 730c by 135 degrees. This disproportionate spacing may be undesirable because the region of the elongated member 700 having the smaller spacing may be overly rigid and/or the region having the larger spacing may be overly flexible.

Figure 8:
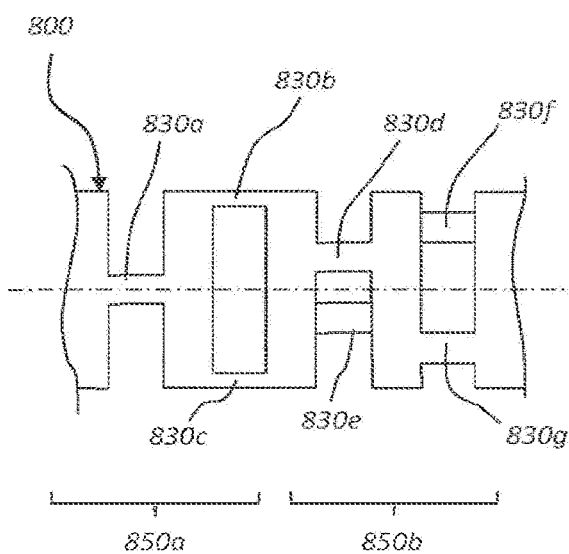

In contrast, a more limited jump in the rotational offset applied from one segment to the next will minimize the discrepancy in beam spacing between segments. For example, FIG. 8 illustrates a section of an elongated member 800 with a more limited rotational offset of about 20 degrees applied between a first segment 850a and a second segment 850b. As in the elongated member 700 of FIG. 7, the first segment 850a includes a first pair of beams 830a and a second pair of beams 830b and 830c, and the second segment 850b includes a first pair of beams 830d and 830e and a second pair of beams 830f and 830g. However, because the second segment 850b is offset from the first segment 850a by a more limited 20 degrees, the spacing discrepancy between beams 830b, 830c, 830d, and 830e is less pronounced. Beam 830d is spaced 70 degrees from beam 830b, and beam 830e is spaced 110 degrees from beam 830b. Likewise, beam 830e is spaced 70 degrees from beam 830c and beam 830d is spaced 110 degrees from beam 830c. Thus, although a spacing discrepancy still exists between segments, it may be controlled to a suitable degree by providing an appropriate rotational offset limit.

The terms "approximately," "about," and "substantially" as used herein represent an amount or condition close to the stated amount or condition that still performs a desired function or achieves a desired result. For example, the terms "approximately," "about," and "substantially" may refer to an amount or condition that deviates by less than 10%, or by less than 5%, or by less than 1%, or by less than 0.1%, or by less than 0.01% from a stated amount or condition.

The present invention may be embodied in other forms, without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An interventional device, comprising:
    an elongated member having a wall and an interior lumen, the elongated member including a plurality of fenestrations extending through the wall and exposing the lumen, the plurality of fenestrations defining a plurality of axially extending beams and a plurality of circumferentially extending rings arranged in an imperfect ramp pattern,
    wherein no set of three successive segments within the imperfect ramp pattern are spaced according to the same rotational offset, and
    wherein the imperfect ramp pattern includes an imperfect rotational offset from one segment to the next, the imperfect rotational offset being equal to a constant value±a variable modifying value,
    wherein the elongated member is formed from a succession of segments, each segment including a first pair of circumferentially opposed beams and a second pair of circumferentially opposed beams which are rotationally offset by about 90 degrees from the first pair of beams.

2. The device of claim 1, wherein the interventional device is a micro-catheter device or a guidewire device.

3. The device of claim 2, wherein the interventional device is a guidewire that includes a core, and wherein the elongated member is formed as a tube structure coupled to the core such that a distal section of the core passes into at least a portion of the tube structure.

4. The device of claim 3, further comprising one or more coils disposed within the tube structure so as to be positioned between an outer surface of the distal section of the core and an inner surface of the tube structure.

5. The device of claim 3, wherein the core is formed from stainless steel or nitinol.

6. The device of claim 3, wherein the tube structure is formed from nitinol.

7. The device of claim 1, wherein the fenestrations are arranged in one or more of a one-beam, two-beam, or three-beam pattern.

8. The device of claim 1, wherein the constant value is about 90 degrees.

9. The device of claim 1, wherein the constant value ranges from 81 degrees to 99 degrees.

10. The device of claim 1, wherein the variable modifying value ranges from 2.5 to 30 degrees.

11. The device of claim 1, wherein the variable modifying value ranges from 5 to 15 degrees.

12. An interventional device, comprising:
    an elongated member having a wall and an interior lumen, the elongated member including a plurality of fenestrations extending through the wall and exposing the lumen, the plurality of fenestrations defining a plurality of axially extending beams and a plurality of circumferentially extending rings arranged in an imperfect ramp pattern,
    wherein no set of three successive segments or beam pairs within the imperfect ramp pattern are spaced according to the same rotational offset,
    wherein the imperfect ramp pattern includes an imperfect rotational offset from one segment to the next or from one beam pair to the next, the imperfect rotational offset being equal to a constant value±a variable modifying value,
    wherein the constant value ranges from 81 degrees to 99 degrees, and
    wherein the variable modifying value ranges from 2.5 to 30 degrees.

13. The device of claim 12, wherein the device is a micro-catheter device or a guidewire device.

14. The device of claim 13, wherein the interventional device is a guidewire that includes a core, and wherein the elongated member is formed as a tube structure coupled to the core such that a distal section of the core passes into at least a portion of the tube structure.

15. The device of claim 14, further comprising one or more coils disposed within the tube structure so as to be positioned between an outer surface of the distal section of the core and an inner surface of the tube structure.

16. The device of claim 14, wherein the core is formed from stainless steel or nitinol.

17. The device of claim 14, wherein the tube structure is formed from nitinol.

* * * * *